(12) United States Patent
Thompson

(10) Patent No.: US 11,891,429 B2
(45) Date of Patent: Feb. 6, 2024

(54) METHODS FOR REGULATING ENDOGENOUS PRODUCTION OF LACTOFERRIN AND SUB-PEPTIDES THEREOF

(71) Applicant: Cellastra Inc., San Francisco, CA (US)

(72) Inventor: Bradley G. Thompson, Calgary (CA)

(73) Assignee: Cellastra Inc., San Francisco, CA (US)

( * ) Notice: Subject to any disclaimer, the term of this patent is extended or adjusted under 35 U.S.C. 154(b) by 68 days.

(21) Appl. No.: 17/320,661

(22) Filed: May 14, 2021

(65) Prior Publication Data

US 2021/0269508 A1    Sep. 2, 2021

Related U.S. Application Data

(63) Continuation of application No. 16/037,769, filed on Jul. 17, 2018, now abandoned.

(51) Int. Cl.
| | |
|---|---|
| *C12N 15/79* | (2006.01) |
| *C07H 21/04* | (2006.01) |
| *C07K 14/79* | (2006.01) |
| *A61K 31/198* | (2006.01) |
| *A61P 17/02* | (2006.01) |
| *A61K 48/00* | (2006.01) |
| *C12N 15/69* | (2006.01) |
| *A61K 38/40* | (2006.01) |
| *C12N 15/86* | (2006.01) |

(52) U.S. Cl.
CPC .......... *C07K 14/79* (2013.01); *A61K 31/198* (2013.01); *A61K 48/0058* (2013.01); *A61K 48/0066* (2013.01); *A61P 17/02* (2018.01); *C12N 15/69* (2013.01); *A61K 38/40* (2013.01); *C07H 21/04* (2013.01); *C12N 15/86* (2013.01)

(58) Field of Classification Search
CPC ........ C12N 15/85; C12N 15/86; A61K 38/00; A61K 38/40; C07H 21/04
See application file for complete search history.

(56) References Cited

U.S. PATENT DOCUMENTS

| | | |
|---|---|---|
| 2006/0094082 A1 | 5/2006 | Varadhachary et al. |
| 2012/0010150 A1 | 1/2012 | Engelmayer et al. |
| 2015/0190425 A1 | 7/2015 | Goolsbee et al. |

FOREIGN PATENT DOCUMENTS

| | | | |
|---|---|---|---|
| CA | 2871468 A1 | * | 10/2013 |
| WO | 2007022537 A2 | | 2/2007 |
| WO | 2011150395 A2 | | 4/2012 |
| WO | WO 2016/210328 A1 | * | 12/2016 |

OTHER PUBLICATIONS

Gray et al., 2011, Adeno-Associated Virus, Methods and Protocols, Chapter 2 "Design and Construction of Functional AAV Vecotrs", Edited by Richard Snyder and Philippe Moullier, Humana Press, Springer Science + Business Media, LLC, 2011, pp. 25-46.*
Bennet et al., 2009, Geneseq Accession No. AXR77954, computer printout, p. 1.*
Chalberg et al., 2013, Geneseq Accession No. BAY70789, computer printout, p. 1.*
Cho et al., 2010, Geneseq Accession No. AXW34336, computer printout, p. 1-2.*
Akira et al., 1986 (Geneseq Accession No. AAN60256, computer printout, pp. 1-2) (Akira-CH2).*
Akira et al., 1986 (Geneseq Accession No. AAN60257, computer printout, pp. 1-2) (Akira-CH3).*
De Romeuf et al., 2015 (Geneseq Accession No. BBZ08461, computer printout, pp. 1-2).*
Earley et al., "Adeno-associated Virus (AAV) Assembly-Activating Protein Is Not an Essential Requirement for Capsid Assembly AAV Serotypes 4, 5, and 11," J Virol., 91(3):e01980-16, Feb. 2017.
International Search Report and Written Opinion of the ISA/US in PCT/US2019/041840, dated Nov. 1, 2019; 10pgs.
Rosa et al., "Lactoferrin: A Natural Glycoprotein Involved in Iron and Inflammatory Homeostasis," Int J Mol Sci., 18(9): E1985, Sep. 2017.
Sanchez et al., "Biological Role of Lactoferrin," Arch Dis Child., 67(5):657-661, May 1992.
Zinn et al., "Adeno-associated Virus: Fit to Serve," Curr Opin Virol., 0:90-97, Oct. 2014.

* cited by examiner

*Primary Examiner* — Shin Lin Chen
(74) *Attorney, Agent, or Firm* — Haukaas Fortius PLLC; Michael Haukaas

(57) ABSTRACT

The present disclosure relates to the composition of one or more agents, therapies, treatments, and methods of use of the agents and/or therapies and/or treatments for upregulating production of lactoferrin or a sub-peptide of lactoferrin. Embodiments of the present disclosure can be used as a therapy or a treatment of adhesions or scarring.

14 Claims, 3 Drawing Sheets

Specification includes a Sequence Listing.

SEQUENCE LISTING

<160> NUMBER OF SEQ ID NOS: 15

<210> SEQ ID NO 1
<211> LENGTH: 711
<212> TYPE: PRT
<213> ORGANISM: Homo sapiens

<400> SEQUENCE: 1

```
Met Lys Leu Val Phe Leu Val Leu Leu Phe Leu Gly Ala Leu Gly Leu
1               5                   10                  15

Cys Leu Ala Gly Arg Arg Arg Ser Val Gln Trp Cys Ala Val Ser
            20                  25                  30

Gln Pro Glu Ala Thr Lys Cys Phe Gln Trp Gln Arg Asn Met Arg Arg
        35                  40                  45

Val Arg Gly Pro Pro Val Ser Cys Ile Lys Arg Asp Ser Pro Ile Gln
    50                  55                  60

Cys Ile Gln Ala Ile Ala Glu Asn Arg Ala Asp Ala Val Thr Leu Asp
65                  70                  75                  80

Gly Gly Phe Ile Tyr Glu Ala Gly Leu Ala Pro Tyr Lys Leu Arg Pro
                85                  90                  95

Val Ala Ala Glu Val Tyr Gly Thr Glu Arg Gln Pro Arg Thr His Tyr
            100                 105                 110

Tyr Ala Val Ala Val Val Lys Lys Gly Gly Ser Phe Gln Leu Asn Glu
        115                 120                 125

Leu Gln Gly Leu Lys Ser Cys His Thr Gly Leu Arg Arg Asn Ala Gly
    130                 135                 140

Trp Asn Val Pro Ile Gly Thr Leu Arg Pro Phe Leu Asn Trp Thr Gly
145                 150                 155                 160

Pro Pro Glu Pro Ile Glu Ala Ala Val Ala Arg Phe Phe Ser Ala Ser
                165                 170                 175

Cys Val Pro Gly Ala Asp Lys Gly Gln Phe Pro Asn Leu Cys Arg Leu
            180                 185                 190

Cys Ala Gly Thr Gly Glu Asn Lys Cys Ala Phe Ser Ser Gln Glu Pro
        195                 200                 205

Tyr Phe Ser Tyr Ser Gly Ala Phe Lys Cys Leu Arg Asp Gly Ala Gly
    210                 215                 220

Asp Val Ala Phe Ile Arg Glu Ser Thr Val Phe Glu Asp Leu Ser Asp
225                 230                 235                 240

Glu Ala Glu Arg Asp Glu Tyr Glu Leu Leu Cys Pro Asp Asn Thr Arg
                245                 250                 255

Lys Pro Val Asp Lys Phe Lys Asp Cys His Leu Ala Arg Val Pro Ser
            260                 265                 270

His Ala Val Val Ala Arg Ser Val Asn Gly Lys Glu Asp Ala Ile Trp
        275                 280                 285

Asn Leu Leu Arg Gln Ala Gln Glu Lys Phe Gly Lys Asp Lys Ser Pro
    290                 295                 300

Lys Phe Gln Leu Phe Gly Ser Pro Ser Gly Gln Lys Asp Leu Leu Phe
305                 310                 315                 320
```

-continued

Lys Asp Ser Ala Ile Gly Phe Ser Arg Val Pro Pro Arg Ile Asp Ser
            325                 330                 335

Gly Leu Tyr Leu Gly Ser Gly Tyr Phe Thr Ala Ile Gln Asn Leu Arg
            340                 345                 350

Lys Ser Glu Glu Glu Val Ala Ala Arg Arg Ala Arg Val Val Trp Cys
            355                 360                 365

Ala Val Gly Glu Gln Glu Leu Arg Lys Cys Asn Gln Trp Ser Gly Leu
            370                 375                 380

Ser Glu Gly Ser Val Thr Cys Ser Ser Ala Ser Thr Thr Glu Asp Cys
385                 390                 395                 400

Ile Ala Leu Val Leu Lys Gly Glu Ala Asp Ala Met Ser Leu Asp Gly
            405                 410                 415

Gly Tyr Val Tyr Thr Ala Gly Lys Cys Gly Leu Val Pro Val Leu Ala
            420                 425                 430

Glu Asn Tyr Lys Ser Gln Gln Ser Ser Asp Pro Asp Pro Asn Cys Val
            435                 440                 445

Asp Arg Pro Val Glu Gly Tyr Leu Ala Val Ala Val Val Arg Arg Ser
            450                 455                 460

Asp Thr Ser Leu Thr Trp Asn Ser Val Lys Gly Lys Lys Ser Cys His
465                 470                 475                 480

Thr Ala Val Asp Arg Thr Ala Gly Trp Asn Ile Pro Met Gly Leu Leu
            485                 490                 495

Phe Asn Gln Thr Gly Ser Cys Lys Phe Asp Glu Tyr Phe Ser Gln Ser
            500                 505                 510

Cys Ala Pro Gly Ser Asp Pro Arg Ser Asn Leu Cys Ala Leu Cys Ile
            515                 520                 525

Gly Asp Glu Gln Gly Glu Asn Lys Cys Val Pro Asn Ser Asn Glu Arg
            530                 535                 540

Tyr Tyr Gly Tyr Thr Gly Ala Phe Arg Cys Leu Ala Glu Asp Ala Gly
545                 550                 555                 560

Asp Val Ala Phe Val Lys Gly Val Thr Val Leu Gln Asn Thr Asp Gly
            565                 570                 575

Asn Asn Asn Glu Ala Trp Ala Lys Asp Leu Lys Leu Ala Asp Phe Ala
            580                 585                 590

Leu Leu Cys Leu Asp Gly Lys Arg Lys Pro Val Thr Glu Ala Arg Ser
            595                 600                 605

Cys His Leu Ala Met Ala Pro Asn His Ala Val Val Ser Arg Met Asp
            610                 615                 620

Lys Val Glu Arg Leu Lys Gln Val Leu Leu His Gln Gln Ala Lys Phe
625                 630                 635                 640

Gly Arg Asn Gly Ser Asp Cys Pro Asp Lys Phe Cys Leu Phe Gln Ser
            645                 650                 655

Glu Thr Lys Asn Leu Leu Phe Asn Asp Asn Thr Glu Cys Leu Ala Arg
            660                 665                 670

Leu His Gly Lys Thr Thr Tyr Glu Lys Tyr Leu Gly Pro Gln Tyr Val
            675                 680                 685

Ala Gly Ile Thr Asn Leu Lys Lys Cys Ser Thr Ser Pro Leu Leu Glu
            690                 695                 700

Ala Cys Glu Phe Leu Arg Lys
705                 710

<210> SEQ ID NO 2
<211> LENGTH: 130

```
<212> TYPE: DNA
<213> ORGANISM: Artificial Sequence
<220> FEATURE:
<223> OTHER INFORMATION: Synthetic Sequence

<400> SEQUENCE: 2
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct                                                          130

<210> SEQ ID NO 3
<211> LENGTH: 128
<212> TYPE: DNA
<213> ORGANISM: Artificial Sequence
<220> FEATURE:
<223> OTHER INFORMATION: Synthetic Sequence

<400> SEQUENCE: 3
aggaacccct agtgatggag ttggccactc cctctctgcg cgctcgctcg ctcactgagg    60
ccgggcgacc aaaggtcgcc cgacgcccgg gctttgcccg ggcggcctca gtgagcgagc   120
gagcgcgc                                                            128

<210> SEQ ID NO 4
<211> LENGTH: 25
<212> TYPE: PRT
<213> ORGANISM: Homo sapiens

<400> SEQUENCE: 4

Glu Ala Thr Lys Cys Phe Gln Trp Gln Arg Asn Met Arg Arg Val Arg
1               5                   10                  15

Gly Pro Pro Val Ser Cys Ile Lys Arg
            20                  25

<210> SEQ ID NO 5
<211> LENGTH: 110
<212> TYPE: PRT
<213> ORGANISM: Artificial Sequence
<220> FEATURE:
<223> OTHER INFORMATION: Synthetic Sequence

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110

<210> SEQ ID NO 6
<211> LENGTH: 107
<212> TYPE: PRT
<213> ORGANISM: Artificial Sequence
```

<220> FEATURE:
<223> OTHER INFORMATION: Synthetic Sequence

<400> SEQUENCE: 6

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 7
<211> LENGTH: 217
<212> TYPE: PRT
<213> ORGANISM: Artificial Sequence
<220> FEATURE:
<223> OTHER INFORMATION: Synthetic Sequence

<400> SEQUENCE: 7

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 8
<211> LENGTH: 807
<212> TYPE: DNA
<213> ORGANISM: Artificial Sequence
<220> FEATURE:
<223> OTHER INFORMATION: Synthetic Sequence

<400> SEQUENCE: 8

| | | |
|---|---|---|
| gaggctacca agtgttttca gtggcagagg aacatgagaa aggtgcgggg accacccgtg | 60 |
| agctgcatca agaggggatc cggaggagga ggcagcggag gaggcggatc tggcggaggc | 120 |
| ggaagcgaca agacccacac atgcccacca tgtcctgctc cagagctgct gggaggacct | 180 |
| tccgtgttcc tgtttcctcc aaagccaaag gatacccctga tgatcagcag gaccccagag | 240 |
| gtgacatgcg tggtggtgga cgtgtcccac gaggaccccg aggtgaagtt caactggtac | 300 |
| gtggacggcg tggaggtgca caacgctaag acaaagccac gcgaggagca gtacaactcc | 360 |
| acctacaggg tggtgtctgt gctgacagtg ctgcaccagg attggctgaa cggaaaggag | 420 |
| tacaagtgca aggtgtctaa caaggccctg cccgctccta tcgagaagac catcagcaag | 480 |
| gccaagggcc agccaagaga gccccaggtg tacacactgc ccccttcccg ggaggagatg | 540 |
| accaagaacc aggtgtctct gacatgtctg gtgaagggat ctaccccctc tgacatcgct | 600 |
| gtggagtggg agagcaacgg ccagcctgag aacaactaca agaccacacc cccgtgctg | 660 |
| gactccgatg gatctttctt tctgtacagc aagctgaccg tggataagtc cagatggcag | 720 |
| cagggcaacg tgtttagctg ctccgtgatg cacgaggccc tgcacaacca ctacacacag | 780 |
| aagtctctga gcctgtcccc cggcaag | 807 |

<210> SEQ ID NO 9
<211> LENGTH: 26
<212> TYPE: PRT
<213> ORGANISM: Artificial Sequence
<220> FEATURE:
<223> OTHER INFORMATION: Synthetic Sequence

<400> SEQUENCE: 9

Met Ala Thr Gly Ser Arg Thr Ser Leu Leu Leu Ala Phe Gly Leu Leu
1               5                   10                  15
Cys Leu Pro Trp Leu Gln Glu Gly Ser Ala
            20                  25

<210> SEQ ID NO 10
<211> LENGTH: 885
<212> TYPE: DNA
<213> ORGANISM: Artificial Sequence
<220> FEATURE:
<223> OTHER INFORMATION: Synthetic Sequence

<400> SEQUENCE: 10

| | | |
|---|---|---|
| atggccaccg gctctcgcac aagcctgctg ctggctttcg gactgctgtg cctgccttgg | 60 |
| ctccaggagg gctccgccga ggctaccaag tgttttcagt ggcagaggaa catgagaaag | 120 |
| gtgcggggac acccgtgag ctgcatcaag aggggatccg gaggaggagg cagcggagga | 180 |
| ggcggatctg gcggaggcgg aagcgacaag acccacacat gcccaccatg tcctgctcca | 240 |
| gagctgctgg gaggacctcc gtgttcctg tttcctccaa agccaaagga tacccctgatg | 300 |
| atcagcagga ccccagaggt gacatgcgtg gtggtggacg tgtcccacga ggaccccgag | 360 |
| gtgaagttca ctggtacgt ggacggcgtg gaggtgcaca acgctaagac aaagccacgc | 420 |
| gaggagcagt acaactccac ctacagggtg gtgtctgtgc tgacagtgct gcaccaggat | 480 |

```
tggctgaacg gaaaggagta caagtgcaag gtgtctaaca aggccctgcc cgctcctatc    540
gagaagacca tcagcaaggc caagggccag ccaagagagc cccaggtgta cacactgccc    600
ccttcccggg aggagatgac caagaaccag gtgtctctga catgtctggt gaagggattc    660 taccccctctg acatcgctgt ggagtgggag agcaacggcc agcctgagaa caactacaag    720
accacaccac ccgtgctgga ctccgatgga tctttctttc tgtacagcaa gctgaccgtg    780
gataagtcca gatggcagca gggcaacgtg tttagctgct ccgtgatgca cgaggccctg    840
cacaaccact acacacagaa gtctctgagc ctgtcccccg gcaag                     885
```

```
<210> SEQ ID NO 11
<211> LENGTH: 1055
<212> TYPE: DNA
<213> ORGANISM: Artificial Sequence
<220> FEATURE:
<223> OTHER INFORMATION: Synthetic Sequence

<400> SEQUENCE: 11
ggagttccgc gttacataac ttacggtaaa tggcccgcct ggctgaccgc ccaacgaccc     60
ccgcccattg acgtcaataa tgacgtatgt tcccatagta acgccaatag ggactttcca   120
ttgacgtcaa tgggtggagt atttacggta aactgcccac ttggcagtac atcaagtgta   180
tcatatgcca agtacgcccc ctattgacgt caatgacggt aaatggcccg cctggcatta   240
tgcccagtac atgaccttat gggactttcc tacttggcag tacatctacg tattagtcat   300
cgctattacc atggtcgagg tgagccccac gttctgcttc actctcccca tctccccccc   360
ctccccaccc ccaattttgt atttatttat tttttaatta ttttgtgcag cgatgggggc   420 ggggggggggg ggggcgcgc gccaggcggg gcggggcggg gcgaggggcg gggcggggcg   480
aggcggagag gtgcggcggc agccaatcag agcggcgcgc tccgaaagtt cctttttatg   540
gcgaggcggc ggcggcggcg gccctataaa aagcgaagcg cgcggcgggc gggagtcgct   600
gcgcgctgcc ttcgccccgt gccccgctcc gccgccgcct cgcgccgccc gccccggctc   660
tgactgaccg cgttactaaa acaggtaagt ccggcctccg cgccgggttt ggcgcctcc    720 cgcgggcgcc cccctcctca cggcgagcgc tgccacgtca gacgaagggc gcagcgagcg   780
tcctgatcct tccgcccgga cgctcaggac agcggcccgc tgctcataag actcggcctt   840
agaaccccag tatcagcaga aggacatttt aggacgggac ttgggtgact ctagggcact   900
ggttttcttt ccagagagcg gaacaggcga ggaaaagtag tcccttctcg gcgattctgc   960
ggagggatct ccgtggggcg gtgaacgccg atgatgcctc tactaaccat gttcatgttt   1020 tcttttttt tctacaggtc ctgggtgacg aacag                                1055
```

```
<210> SEQ ID NO 12
<211> LENGTH: 589
<212> TYPE: DNA
<213> ORGANISM: Artificial Sequence
<220> FEATURE:
<223> OTHER INFORMATION: Synthetic Sequence

<400> SEQUENCE: 12
aatcaacctc tggattacaa aatttgtgaa agattgactg gtattcttaa ctatgttgct     60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga cttttcgcttt ccccctccct   300
```

| | |
|---|---|
| attgccacgg cggaactcat cgccgcctgc cttgcccgct gctggacagg ggctcggctg | 360 |
| ttgggcactg acaattccgt ggtgttgtcg gggaaatcat cgtcctttcc ttggctgctc | 420 |
| gcctgtgttg ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgc | 589 |

<210> SEQ ID NO 13
<211> LENGTH: 6749
<212> TYPE: DNA
<213> ORGANISM: Artificial Sequence
<220> FEATURE:
<223> OTHER INFORMATION: Synthetic Sequence

<400> SEQUENCE: 13

| | |
|---|---|
| cagcagctgc gcgctcgctc gctcactgag gccgcccggg caaagcccgg gcgtcgggcg | 60 |
| acctttggtc gcccggcctc agtgagcgag cgagcgcgca gagagggagt ggccaactcc | 120 |
| atcactaggg gttccttgta gttaatgatt aacccgccat gctacttatc tacgtagcca | 180 |
| tgctctagga cattgattat tgactagtgg agttccgcgt tacataactt acggtaaatg | 240 |
| gcccgcctgg ctgaccgccc aacgaccccc gcccattgac gtcaataatg acgtatgttc | 300 |
| ccatagtaac gccaataggg actttccatt gacgtcaatg ggtggagtat ttacggtaaa | 360 |
| ctgcccactt ggcagtacat caagtgtatc atatgccaag tacgccccct attgacgtca | 420 |
| atgacggtaa atggcccgcc tggcattatg cccagtacat gaccttatgg gactttccta | 480 |
| cttggcagta catctacgta ttagtcatcg ctattaccat ggtcgaggtg agccccacgt | 540 |
| tctgcttcac tctccccatc tcccccccct ccccaccccc aatttgtat ttatttattt | 600 |
| tttaattatt ttgtgcagcg atggggggcgg ggggggggggg gggcgcgcgc caggcggggc | 660 |
| ggggcgggggc gaggggcggg gcggggcgag gcggagaggt gcggcggcag ccaatcagag | 720 |
| cggcgcgctc cgaaagtttc cttttatggc gaggcggcgg cggcggcggc cctataaaaa | 780 |
| gcgaagcgcg cggcgggcgg gagtcgctgc gcgctgcctt cgccccgtgc ccgctccgc | 840 |
| cgccgcctcg cgccgcccgc cccggctctg actgaccgcg ttactaaaac aggtaagtcc | 900 |
| ggcctccgcg ccgggttttg gcgcctcccg cgggcgcccc cctcctcacg gcgagcgctg | 960 |
| ccacgtcaga cgaagggcgc agcgagcgtc ctgatccttc cgcccggacg ctcaggacag | 1020 |
| cggcccgctg ctcataagac tcggccttag aaccccagta tcagcagaag gacattttag | 1080 |
| gacgggactt gggtgactct agggcactgg ttttctttcc agagagcgga acaggcgagg | 1140 |
| aaaagtagtc ccttctcggc gattctgcgg agggatctcc gtgggcggt gaacgccgat | 1200 |
| gatgcctcta ctaaccatgt tcatgttttc tttttttttc tacaggtcct gggtgacgaa | 1260 |
| cagggtaccg ccaccatggc caccggctct cgcacaagcc tgctgctggc tttcggactg | 1320 |
| ctgtgcctgc cttggctcca ggagggctcc gccgaggcta ccaagtgttt tcagtggcag | 1380 |
| aggaacatga gaaggtgcg gggaccaccc gtgagctgca tcaagagggg atccggagga | 1440 |
| ggaggcagcg gaggaggcgg atctggcgga ggcggaagcg acaagaccca cacatgccca | 1500 |
| ccatgtcctg ctccagagct gctgggagga ccttccgtgt tcctgttcc tccaaagcca | 1560 |
| aaggataccc tgatgatcag caggacccca gaggtgacat gcgtggtggt ggacgtgtcc | 1620 |
| cacgaggacc ccgaggtgaa gttcaactgg tacgtgacg gcgtggaggt gcacaacgct | 1680 |
| aagacaaagc cacgcgagga gcagtacaac tccacctaca gggtggtgtc tgtgctgaca | 1740 |

```
gtgctgcacc aggattggct gaacggaaag gagtacaagt gcaaggtgtc taacaaggcc      1800
ctgcccgctc ctatcgagaa gaccatcagc aaggccaagg gccagccaag agagccccag      1860
gtgtacacac tgcccccttc ccgggaggag atgaccaaga accaggtgtc tctgacatgt      1920
ctggtgaagg gattctaccc ctctgacatc gctgtggagt gggagagcaa cggccagcct      1980
gagaacaact acaagaccac accacccgtg ctggactccg atggatcttt ctttctgtac      2040
agcaagctga ccgtggataa gtccagatgg cagcagggca acgtgtttag ctgctccgtg      2100
atgcacgagg ccctgcacaa ccactacaca cagaagtctc tgagcctgtc ccccggcaag      2160
tgactctaga ataatcaacc tctggattac aaaatttgtg aaagattgac tggtattctt      2220
aactatgttg ctccttttac gctatgtgga tacgctgctt aatgcctttt gtatcatgct      2280
attgcttccc gtatggcttt cattttctcc tccttgtata atcctggtt gctgtctctt      2340 tatgaggagt tgtggcccgt tgtcaggcaa cgtggcgtgg tgtgcactgt gtttgctgac      2400
gcaaccccca ctggttgggg cattgccacc acctgtcagc tcctttccgg actttcgct      2460 ttccccctcc ctattgccac ggcggaactc atcgccgcct gccttgcccg ctgctggaca      2520
ggggctcggc tgttgggcac tgacaattcc gtggtgttgt cggggaaatc atcgtccttt      2580
ccttggctgc tcgcctgtgt tgccacctgg attctgcgcg gacgtccctt ctgctacgtc      2640
ccttcggccc tcaatccagc ggaccttcct tcccgcggcc tgctgccggc tctgcggcct      2700
cttccgcgtc ttcgccttcg ccctcagacg agtcggatct ccctttgggc cgcctccccg      2760
cctaagctta tcgataccgt cgagatctaa cttgtttatt gcagcttata atggttacaa      2820
ataaagcaat agcatcacaa atttcacaaa taaagcattt ttttcactgc attctagttg      2880
tggtttgtcc aaactcatca atgtatctta tcatgtctgg atctcgacct cgactagagc      2940
atggctacgt agataagtag catggcgggt taatcattaa ctacaaggaa ccctagtga      3000 tggagttggc cactccctct ctgcgcgctc gctcgctcac tgaggccggg cgaccaaagg      3060
tcgcccgacg cccgggcttt gcccgggcgg cctcagtgag cgagcgagcg cgcagctgg      3120 cgtaatagcg aagaggcccg caccgatcgc ccttcccaac agttgcgcag cctgaatggc      3180
gaatggaatt ccagacgatt gagcgtcaaa atgtaggtat ttccatgagc gttttttcctg      3240 ttgcaatggc tggcggtaat attgttctgg atattaccag caaggccgat agtttgagtt      3300
cttctactca ggcaagtgat gttattacta atcaaagaag tattgcgaca acggttaatt      3360
tgcgtgatgg acagactctt ttactcggtg gcctcactga ttataaaaac acttctcagg      3420
attctggcgt accgttcctg tctaaaatcc ctttaatcgg cctcctgttt agctcccgct      3480
ctgattctaa cgaggaaagc acgttatacg tgctcgtcaa agcaaccata gtacgcgccc      3540
tgtagcggcg cattaagcgc ggcgggtgtg tggttacgc gcagcgtgac cgctacactt      3600
gccagcgccc tagcgcccgc tcctttcgct ttcttccctt cctttctcgc cacgttcgcc      3660
ggctttcccc gtcaagctct aaatcggggg ctccctttag ggttccgatt tagtgcttta      3720
cggcacctcg accccaaaaa acttgattag ggtgatggtt cacgtagtgg gccatcgccc      3780
tgatagacgg ttttcgccc tttgacgttg gagtccacgt tctttaatag tggactcttg      3840
ttccaaactg gaacaacact caaccctatc tcggtctatt cttttgattt ataagggatt      3900
ttgccgattt cggcctattg gttaaaaaat gagctgattt aacaaaaatt taacgcgaat      3960
tttaacaaaa tattaacgtt tacaatttaa atatttgctt atacaatctt cctgtttttg      4020
gggcttttct gattatcaac cggggtacat atgattgaca tgctagtttt acgattaccg      4080
ttcatcgatt ctcttgtttg ctccagactc tcaggcaatg acctgatagc ctttgtagag      4140
```

```
acctctcaaa aatagctacc ctctccggca tgaatttatc agctagaacg gttgaatatc    4200
atattgatgg tgatttgact gtctccggcc tttctcaccc gtttgaatct ttacctacac    4260
attactcagg cattgcattt aaaatatatg agggttctaa aaattttat ccttgcgttg     4320 aaataaaggc ttctcccgca aaagtattac agggtcataa tgttttggt acaaccgatt     4380 tagctttatg ctctgaggct ttattgctta attttgctaa ttctttgcct tgcctgtatg    4440
atttattgga tgttggaatt cctgatgcgg tattttctcc ttacgcatct gtgcggtatt    4500
tcacaccgca tatggtgcac tctcagtaca atctgctctg atgccgcata gttaagccag    4560
ccccgacacc cgccaacacc cgctgacgcg ccctgacggg cttgtctgct cccggcatcc    4620
gcttacagac aagctgtgac cgtctccggg agctgcatgt gtcagaggtt ttccaccgtca   4680 tcaccgaaac gcgcgagacg aaagggcctc gtgatacgcc tatttttata ggttaatgtc    4740
atgataataa tggtttctta gacgtcaggt ggcacttttc ggggaaatgt gcgcggaacc    4800
cctatttgtt tatttttcta aatacattca aatatgtatc cgctcatgag acaataaccc    4860
tgataaatgc ttcaataata ttgaaaaagg aagagtatga gtattcaaca tttccgtgtc    4920
gcccttattc ccttttttgc ggcattttgc cttcctgttt ttgctcaccc agaaacgctg    4980
gtgaaagtaa aagatgctga agatcagttg ggtgcacgag tgggttacat cgaactggat    5040
ctcaacagcg gtaagatcct tgagagtttt cgccccgaag aacgttttcc aatgatgagc    5100
acttttaaag ttctgctatg tggcgcggta ttatcccgta ttgacgccgg caagagcaa    5160 ctcggtcgcc gcatacacta ttctcagaat gacttggttg agtactcacc agtcacagaa    5220
aagcatctta cggatggcat gacagtaaga gaattatgca gtgctgccat aaccatgagt    5280
gataacactg cggccaactt acttctgaca acgatcggag gaccgaagga gctaaccgct    5340
tttttgcaca acatggggga tcatgtaact cgccttgatc gttgggaacc ggagctgaat    5400
gaagccatac caaacgacga gcgtgacacc acgatgcctg tagcaatggc aacaacgttg    5460
cgcaaactat taactggcga actacttact ctagcttccc ggcaacaatt aatagactgg    5520
atggaggcgg ataaagttgc aggaccactt ctgcgctcgg cccttccggc tggctggttt    5580
attgctgata atctggagc cggtgagcgt gggtctcgcg gtatcattgc agcactgggg    5640
ccagatggta agccctcccg tatcgtagtt atctacacga cggggagtca ggcaactatg    5700
gatgaacgaa atagacagat cgctgagata ggtgcctcac tgattaagca ttggtaactg    5760
tcagaccaag tttactcata tatactttag attgatttaa aacttcattt ttaatttaaa    5820
aggatctagg tgaagatcct ttttgataat ctcatgacca aaatccctta acgtgagttt    5880
tcgttccact gagcgtcaga ccccgtagaa aagatcaaag gatcttcttg agatcctttt    5940
tttctgcgcg taatctgctg cttgcaaaca aaaaaaccac cgctaccagc ggtggtttgt    6000
ttgccggatc aagagctacc aactctttt ccgaaggtaa ctggcttcag cagagcgcag    6060
ataccaaata ctgtccttct agtgtagccg tagttaggcc accacttcaa gaactctgta    6120
gcaccgccta catcctcgc tctgctaatc ctgttaccag tggctgctgc cagtggcgat    6180
aagtcgtgtc ttaccgggtt ggactcaaga cgatagttac cggataaggc gcagcggtcg    6240
ggctgaacgg ggggttcgtg cacacagccc agcttggagc gaacgaccta caccgaactg    6300
agatacctac agcgtgagct atgagaaagc gccacgcttc ccgaagggag aaaggcggac    6360
aggtatccgg taagcggcag ggtcggaaca ggagagcgca cgagggagct tccaggggga    6420
aacgcctggt atctttatag tcctgtcggg tttcgccacc tctgacttga gcgtcgattt    6480
```

```
ttgtgatgct cgtcagggggg gcggagccta tggaaaaacg ccagcaacgc ggcctttta      6540 cggttcctgg cctttttgctg gccttttgct cacatgttct ttcctgcgtt atcccctgat      6600
tctgtggata accgtattac cgcctttgag tgagctgata ccgctcgccg cagccgaacg      6660
accgagcgca gcgagtcagt gagcgaggaa gcggaagagc gcccaatacg caaaccgcct      6720
ctccccgcgc gttggccgat tcattaatg                                        6749
```

<210> SEQ ID NO 14
<211> LENGTH: 269
<212> TYPE: PRT
<213> ORGANISM: Artificial Sequence
<220> FEATURE:
<223> OTHER INFORMATION: Synthetic Sequence

<400> SEQUENCE: 14

```
Glu Ala Thr Lys Cys Phe Gln Trp Gln Arg Asn Met Arg Arg Val Arg
1               5                   10                  15

Gly Pro Pro Val Ser Cys Ile Lys Arg Gly Ser Gly Gly Gly Gly Ser
            20                  25                  30

Gly Gly Gly Gly Ser Gly Gly Gly Ser Asp Lys Thr His Thr Cys
        35                  40                  45

Pro Pro Cys Pro Ala Pro Glu Leu Leu Gly Gly Pro Ser Val Phe Leu
    50                  55                  60

Phe Pro Pro Lys Pro Lys Asp Thr Leu Met Ile Ser Arg Thr Pro Glu
65                  70                  75                  80

Val Thr Cys Val Val Val Asp Val Ser His Glu Asp Pro Glu Val Lys
                85                  90                  95

Phe Asn Trp Tyr Val Asp Gly Val Glu Val His Asn Ala Lys Thr Lys
            100                 105                 110

Pro Arg Glu Glu Gln Tyr Asn Ser Thr Tyr Arg Val Val Ser Val Leu
        115                 120                 125

Thr Val Leu His Gln Asp Trp Leu Asn Gly Lys Glu Tyr Lys Cys Lys
    130                 135                 140

Val Ser Asn Lys Ala Leu Pro Ala Pro Ile Glu Lys Thr Ile Ser Lys
145                 150                 155                 160

Ala Lys Gly Gln Pro Arg Glu Pro Gln Val Tyr Thr Leu Pro Pro Ser
                165                 170                 175

Arg Glu Glu Met Thr Lys Asn Gln Val Ser Leu Thr Cys Leu Val Lys
            180                 185                 190

Gly Phe Tyr Pro Ser Asp Ile Ala Val Glu Trp Glu Ser Asn Gly Gln
        195                 200                 205

Pro Glu Asn Asn Tyr Lys Thr Thr Pro Pro Val Leu Asp Ser Asp Gly
    210                 215                 220

Ser Phe Phe Leu Tyr Ser Lys Leu Thr Val Asp Lys Ser Arg Trp Gln
225                 230                 235                 240

Gln Gly Asn Val Phe Ser Cys Ser Val Met His Glu Ala Leu His Asn
                245                 250                 255

His Tyr Thr Gln Lys Ser Leu Ser Leu Ser Pro Gly Lys
            260                 265
```

<210> SEQ ID NO 15
<211> LENGTH: 295
<212> TYPE: PRT
<213> ORGANISM: Artificial Sequence
<220> FEATURE:
<223> OTHER INFORMATION: Synthetic Sequence

```
<400> SEQUENCE: 15

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Glu Ala Thr Lys Cys Phe
                20                  25                  30

Gln Trp Gln Arg Asn Met Arg Val Arg Gly Pro Pro Val Ser Cys
            35                  40                  45

Ile Lys Arg Gly Ser Gly Gly Gly Ser Gly Gly Gly Ser Gly
    50              55                  60

Gly Gly Ser Asp Lys Thr His Thr Cys Pro Pro Cys Pro Ala Pro
65              70                  75                  80

Glu Leu Leu Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
                100                 105                 110

Asp Val Ser His Glu Asp Pro Glu Val Lys Phe Asn Trp Tyr Val Asp
                115                 120                 125

Gly Val Glu Val His Asn Ala Lys Thr Lys Pro Arg Glu Glu Gln Tyr
    130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
                180                 185                 190

Glu Pro Gln Val Tyr Thr Leu Pro Pro Ser Arg Glu Glu Met Thr Lys
                195                 200                 205

Asn Gln Val Ser Leu Thr Cys Leu Val Lys Gly Phe Tyr Pro Ser Asp
                210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
                260                 265                 270

Cys Ser Val Met His Glu Ala Leu His Asn His Tyr Thr Gln Lys Ser
                275                 280                 285

Leu Ser Leu Ser Pro Gly Lys
    290                 295
```

METHODS FOR REGULATING ENDOGENOUS PRODUCTION OF LACTOFERRIN AND SUB-PEPTIDES THEREOF

CROSS-REFERENCE TO RELATED APPLICATION

This application is a continuation-in-part of U.S. patent application Ser. No. 16/037,769 filed on Jul. 17, 2018, which is hereby incorporated by reference.

SEQUENCE LISTING

This application contains a Sequence Listing electronically submitted via EFS-WEB to the United States Patent and Trademark Office as an ASCII text file entitled "A8141863USCIP_ST25.txt" created on 2021 Apr. 28 and having a size of 29,900 bytes. The information contained in the Sequence Listing is incorporated by reference herein.

TECHNICAL FIELD

The present disclosure generally relates to viral gene vectors engineered to endogenously produce lactoferrin and sub-peptides of lactoferrin. In particular, the present disclosure relates to agents, therapies, and methods of use of the agents and/or therapies for upregulating endogenous production of one or more of lactoferrin and sub-peptides of lactoferrin.

BACKGROUND

Lactoferrin is one of the transferrin proteins that transfer iron to cells and control the level of free iron in the blood and external secretions. Lactoferrin is present in the milk of humans and other mammals, as well as in the blood plasma and neutrophils, and it is one of the major proteins of virtually all exocrine secretions of mammals, such as pancreatic exocrine secretion, saliva, bile, and tears. The concentration of lactoferrin in milk varies from 7 g/L in the colostrum to 1 g/L in mature milk.

SUMMARY

Embodiments of the present disclosure relate to inducing endogenous production of lactoferrin or sub-peptides of lactoferrin utilizing gene vectors that contain nucleotide sequences and/or genes for one or more of lactoferrin and/or sub-peptides of lactoferrin.

Some embodiments of the present disclosure relate to gene vectors, compositions and methods that cause a subject to produce a lactoferrin-Fc fusion peptide. In some embodiments, the lactoferrin-Fc fusion peptide comprises lactoferrin or a sub-peptide of lactoferrin.

In some embodiments of the present disclosure, the gene vectors described herein comprise a vector of plasmid deoxyribonucleic acid (DNA) that includes an insert sequence of nucleic acids. The insert sequence encodes for the production of lactoferrin or a sub-peptide of lactoferrin and the gene vector may also include a backbone sequence of nucleic acids that facilitates introduction of the insert sequence into one or more of a subject's cells. Within the subject's cells, the insert sequence is expressed and/or replicated. Expression of the insert sequence by one or more cells of the subject results in an increased production of the lactoferrin or a sub-peptide of lactoferrin by the subject. In some embodiments, the insert encodes for a lactoferrin-Fc fusion protein, such as for example a fusion protein comprising lactoferrin or a sub-peptide of lactoferrin linked to an immunoglobulin (e.g., an IgG Fc-region).

In some embodiments of the present disclosure, the gene vector is a recombinant virus vector (RVV). In an embodiment, the RVV comprises: a nucleotide sequence encoding a human lactoferrin protein or a sub-peptide thereof linked to an immunoglobulin; and an inverted terminal repeat. In some embodiments, the human lactoferrin protein is of SEQ ID No. 1 and the sub-peptide is any fragment thereof (e.g., SEQ ID No. 4). In some embodiments, the immunoglobulin is a human IgG Fc region comprising the CH2 and CH3 domains of SEQ ID No. 5 and 6, respectively. In some embodiments, the nucleotide sequence encoding the human lactoferrin protein or sub-peptide thereof linked to the immunoglobulin comprises a sequence of SEQ ID No. 8 or a human codon optimized variant thereof. In some embodiments, the RVV further comprises a nucleotide sequence encoding a human growth hormone (HGH) signal peptide, such as a sequence of SEQ ID No. 9. Thus, in some embodiments, the RVV comprises the nucleotide sequence of SEQ ID No. 10 or a human codon optimized variant thereof, encoding a fusion protein comprising a HGH signal peptide, a lactoferrin sub-peptide and a human IgG Fc region.

In some embodiments, the RVV comprises the nucleotide sequence of SEQ ID No. 13 or a human codon optimized variant thereof.

In some embodiments, the present disclosure relates to a fusion protein comprising a human lactoferrin protein or a sub-peptide thereof linked to an immunoglobulin. In some embodiments, the human lactoferrin protein is of SEQ ID No. 1 and the sub-peptide is any fragment thereof (e.g. SEQ ID No. 4). In some embodiments, the immunoglobulin is a human IgG Fc region comprising the CH2 and CH3 domains of SEQ ID No. 5 and 6, respectively. In some embodiments, the fusion peptide comprises the amino acid sequence of SEQ ID No. 14. In some embodiments, the fusion protein further comprises an HGH signal peptide, such as a sequence of SEQ ID No. 9. Thus, in some embodiments, the fusion protein comprises the amino acid sequence of SEQ ID No. 15.

In some embodiments, the present disclosure relates to a composition that comprises a nucleotide sequence according to SEQ ID No. 13 or a human codon optimized variant thereof, that can be expressed in a target cell.

Some embodiments of the present disclosure relate to a method of making an agent/target cell complex, the method comprises a step of administering a therapeutically effective amount of the agent to a subject, wherein the agent/target cell complex may increase the subject's production of one or more of lactoferrin and/or sub-peptides of lactoferrin.

Some embodiments of the present disclosure relate to a method of making an agent/target cell complex, the method comprising a step of administering a sufficient amount of an agent to a target cell whereby the agent/target cell complex is formed, wherein the agent/target cell complex may increase the production of lactoferrin and/or sub-peptides of lactoferrin by said target cell.

In some embodiments, the present disclosure relates to a method of making an agent/target cell complex, the method comprising a step of administering a recombinant virus vector (RVV) to a target cell for forming the agent/target cell complex, wherein the agent/target cell complex causes the target cell to increase a production of a human lactoferrin protein or a sub-peptide thereof. In some embodiments, the RVV comprises the nucleotide sequence of SEQ ID No. 8, 10 or 13, or a human codon optimized variant of any one thereof.

Some embodiments of the present disclosure relate to a pharmaceutical composition that comprises an agent, a pharmaceutically acceptable carrier, and/or an excipient. The agent may upregulate the production of lactoferrin and/or a sub-peptide of lactoferrin.

In some embodiments, the present disclosure relates to a pharmaceutical composition comprising the RVV as described herein and one or more pharmaceutically acceptable carriers and/or one or more excipients.

Some embodiments of the present disclosure relate to a kit used for treatment of a condition or for delivery of a therapy to a subject. The kit comprises a unit dosage of an agent, a carrier for the unit dosage, and instructions for administering the unit dosage to the subject. The agent may upregulate production of lactoferrin and/or a sub-peptide of lactoferrin. The carrier may be a solid carrier, such as a capsule or tablet, or a liquid. The instructions may describe how the solid carrier may be administered to a subject for an optimal effect. The instructions may also describe how the liquid carrier may be administered to a subject by various routes of administration.

Some embodiments of the present disclosure relate to a method of treating a condition. The method comprises a step of administering to a subject a therapeutically effective amount of an agent that upregulates a production of lactoferrin and/or a sub-peptide of lactoferrin.

Without being bound by any particular theory, embodiments of the present disclosure may be useful for treating conditions including adhesions and scarring.

BRIEF DESCRIPTION OF THE DRAWINGS

These and other features of the present disclosure will become more apparent in the following detailed description in which reference is made to the appended drawings.

DETAILED DESCRIPTION

Definitions

Figure 1:
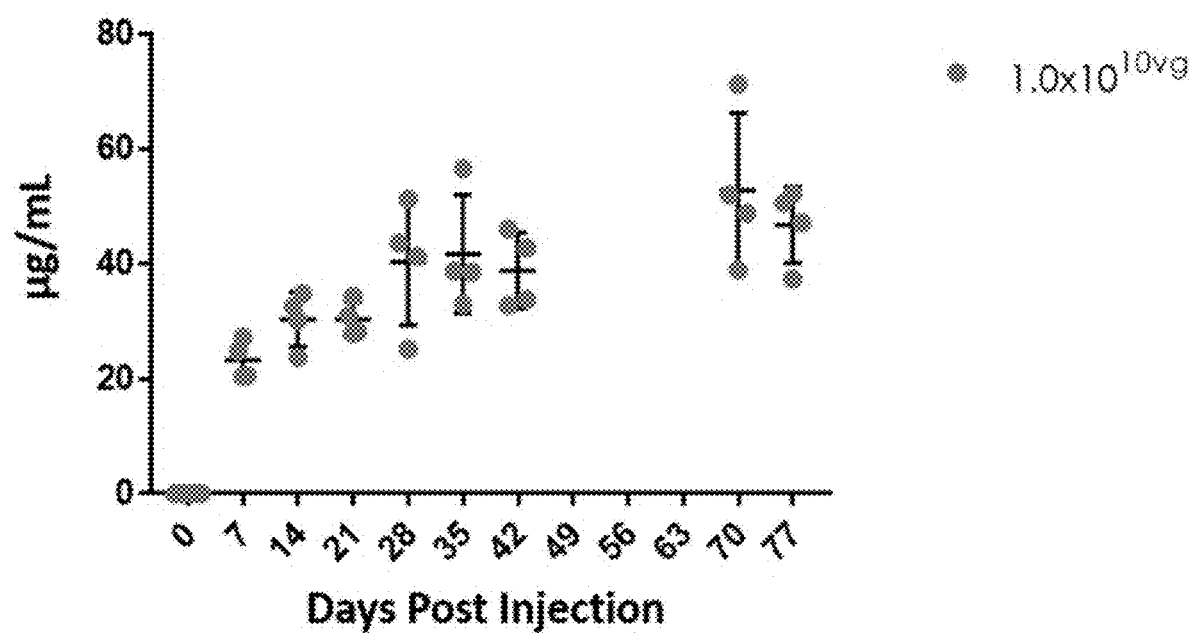
FIG. 1 is a scatter plot that shows lactoferrin-Fc fusion peptide expression in mice following administration of a vector, according to embodiments of the present disclosure, in mice with tumor cells.

Unless defined otherwise, all technical and scientific terms used herein have the meanings that would be commonly understood by one of skill in the art in the context of the present specification. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

As used herein, the singular forms "a", "an", and "the" include plural references unless the context clearly dictates otherwise. For example, reference to "an agent" includes one or more agents and reference to "a subject" or "the subject" includes one or more subjects.

As used herein, the terms "about" or "approximately" refer to within about 25%, preferably within about 20%, of a given value or range. It is understood that such a variation is always included in any given value provided herein, whether or not it is specifically referred to.

As used herein, the term "agent" refers to a substance that, when administered to a patient, causes one or more chemical reactions and/or one or more physical reactions and/or or one or more physiologic reactions in the patient. In an embodiment, the agent is a gene vector, such as for example a recombinant virus vector (RVV) as described herein.

As used herein, the term "ameliorate" refers to an improvement and/or to make better and/or to make more satisfactory.

As used herein, the term "cell" refers to a single cell as well as a plurality of cells or a population of the same cell type or different cell types. Administering an agent to a cell includes in vivo, in vitro and ex vivo administrations or combinations thereof.

As used herein, the term "complex" refers to an association, either direct or indirect, between one or more particles of an agent and one or more target cells. In an embodiment, reference to a complex includes uptake of one or more particles of the agent by the target cell. In further embodiment, reference to a complex include uptake and expression of one or more particles of the agent by the target cell. This association results in a change in the metabolism of the target cell. As used herein, the phrase "change in metabolism" refers to an increase or a decrease in the one or more target cells' production of deoxyribonucleic acid (DNA), ribonucleic acid (RNA), one or more proteins, or any post-translational modifications of one or more proteins.

As used herein, the terms "dysregulation" and "dysregulated" refer to situations or conditions wherein homeostatic control systems have been disturbed and/or compromised so that one or more metabolic, physiologic and/or biochemical systems within a subject operate partially or entirely without said homeostatic control systems.

As used herein, the term "effector molecule" refers to a molecule within a subject that can directly or indirectly regulate the metabolic activity of a target cell by increasing or decreasing the production of DNA, RNA and/or amino-acid sequences and/or by increasing or decreasing any post-translational modifications of one or more proteins.

As used herein, the term "endogenous" refers to the production and/or modification of a molecule that originates within a cell of a subject. In particular, endogenous may refer to expression within a cell of a subject of protein and/or peptides encoded by a gene vector that is delivered to a subject.

As used herein, the term "excipient" refers to any substance, not itself an agent, which may be used as a component within a pharmaceutical composition or a medicament for administration of a therapeutically effective amount of the agent to a subject. Additionally or alternatively, an excipient may alone, or in combination with further chemical components, improve the handling and/or storage properties and/or to permit or facilitate formation of a dose unit of the agent. Excipients include, but are not limited to, one or more of: a binder, a disintegrant, a diluent, a buffer, a solvent, a thickening agent, a gelling agent, a penetration enhancer, a solubilizing agent, a wetting agent, an antioxidant, a preservative, a surface active agent, a lubricant, an emollient, a substance added to improve the appearance or texture of the composition, and a substance used to form the pharmaceutical compositions or medicaments. Any such excipients can be used in any dosage forms according to the present disclosure. The foregoing classes of excipients are not meant to be exhaustive but are provided merely as illustrative of what a person of skill in the art would know; a person of skill in the art would also recognize that additional types and combinations of excipients may be used to achieve delivery of a therapeutically effective amount of the agent to a subject through one or more routes of administration.

As used herein, the terms "inhibit", "inhibiting", and "inhibition" refer to a decrease in activity, response, or other biological parameter of a biologic process, disease, disorder or symptom thereof. This can include but is not limited to the complete ablation of the activity, response, condition, or disease. This may also include, for example, a 10% reduction in the activity, response, condition, or disease as compared to the native or control level. Thus, the reduction can be a 10%, 20%, 30%, 40%, 50%, 60%, 70%, 80%, 90%, 100%, or any amount of reduction in between the specifically recited percentages, as compared to native or control levels.

As used herein, the term "medicament" refers to a medicine and/or pharmaceutical composition that comprises the agent and that can promote recovery from a disease, disorder or symptom thereof and/or that can prevent a disease, disorder or symptom thereof and/or that can inhibit the progression of a disease, disorder, or symptom thereof.

As used herein, the term "patient" refers to a subject that is afflicted with a disease or disorder. The term "patient" includes human and veterinary subjects.

As used herein, the term "pharmaceutical composition" means any composition for administration of the agent to a subject in need of therapy or treatment of a disease, disorder or symptom thereof. Pharmaceutical compositions may include additives such as pharmaceutically acceptable carriers, pharmaceutically accepted salts, excipients and the like. Pharmaceutical compositions may also additionally include one or more further active ingredients such as antimicrobial agents, anti-inflammatory agents, anaesthetics, analgesics, and the like.

As used herein, the term "pharmaceutically acceptable carrier" refers to an essentially chemically inert and non-toxic component within a pharmaceutical composition or medicament that does not inhibit the effectiveness and/or safety of the agent. Some examples of pharmaceutically acceptable carriers and their formulations are described in Remington (1995, The Science and Practice of Pharmacy (19th ed.) ed. A. R. Gennaro, Mack Publishing Company, Easton, Pa.), the disclosure of which is incorporated herein by reference. Typically, an appropriate amount of a pharmaceutically acceptable carrier is used in the formulation to render the formulation isotonic. Examples of suitable pharmaceutically acceptable carriers include, but are not limited to: saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes of various constituents. Such pharmaceutical compositions contain a therapeutically effective amount of the agent, together with a suitable amount of one or more pharmaceutically acceptable carriers and/or excipients so as to provide a form suitable for proper administration to the subject. The formulation should suit the route of administration. For example, oral administration may require that the formulation incorporate enteric coatings to protect the agent from degrading within portions of the subject's gastrointestinal tract. In another example, injectable routes of administration may be administered in a liposomal formulation to facilitate transport throughout a subject's vascular system and to facilitate delivery across cell membranes of targeted intracellular sites.

As used herein, the phrases "prevention of" and "preventing" refer to avoiding an onset or progression of a disease, disorder, or a symptom thereof.

As used herein, the terms "production", "producing" and "produce" refer to the synthesis and/or replication of DNA, the transcription of one or more sequences of RNA, the translation of one or more amino acid sequences, the post-translational modifications of amino acid sequences, and/or the production or functionality of one or more regulatory molecules that can influence the production or functionality of an effector molecule.

As used herein, the terms "promote", "promotion", and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, the increase in an activity, response, condition, disease, or other biological parameter can be 10%, 20%, 30%, 40%, 50%, 60%, 70%, 80%, 90%, 100%, or more, including any amount of increase in between the specifically recited percentages, as compared to native or control levels.

As used herein, the term "prophylactic administration" refers to the administration of any composition to a subject, in the absence of any symptom or indication of a disease or disorder, to prevent the occurrence of and/or the progression of the disease or disorder within the subject.

As used herein, the term "subject" refers to any therapeutic target that receives the agent. The subject can be a vertebrate, for example, a mammal including a human. The term "subject" does not denote a particular age or sex. The term "subject" also refers to one or more cells of an organism; an in vitro culture of one or more tissue types, an in vitro culture of one or more cell types; ex vivo preparations; and a sample of biological materials such as tissue and/or biological fluids.

As used herein, the term "target cell" refers to one or more cells that are deleteriously affected, either directly or indirectly, by a dysregulated immune system.

As used herein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used herein, the term "therapeutically effective amount" refers to the amount of the agent used that is of sufficient quantity to ameliorate, treat and/or inhibit one or more of a disease, disorder or a symptom thereof. The "therapeutically effective amount" will vary depending on the agent used, the route of administration of the agent, and the severity of the disease, disorder or symptom thereof. The subject's age, weight and genetic make-up may also influence the amount of the agent that will be a therapeutically effective amount.

As used herein, the terms "unit dosage form" and "unit dose" refer to a physically discrete unit that is suitable as a unitary dose for patients. Each unit contains a predetermined quantity of the agent and optionally, one or more suitable pharmaceutically acceptable carriers, one or more excipients, one or more additional active-ingredients, or combinations thereof. The amount of agent within each unit is a therapeutically effective amount.

In one embodiment of the present disclosure, the pharmaceutical compositions disclosed herein comprise an agent as described above in a total amount by weight of the composition of about 0.1% to about 95%. For example, the amount of the agent by weight of the pharmaceutical composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95%.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

The present disclosure relates to one or more agents, therapies, treatments and methods of use of the agents and/or therapies and/or treatments for upregulating production of a lactoferrin protein and/or a sub-peptide of lactoferrin.

In some embodiments of the present disclosure, the agent is a plasmid vector or gene vector for introducing into a target cell for expression (e.g., transcription and translation) an insert that comprises one or more nucleotide sequences that are carried within the plasmid vector. In some embodiments of the present disclosure, the plasmid vector is a viral vector. In some embodiments of the present disclosure, the vector is an adeno-associated virus vector. In some embodiments of the present disclosure, the insert for expression is a fusion protein comprising a human lactoferrin protein or a sub-peptide thereof linked to an immunoglobulin.

For the purposes of the present disclosure, the term "lactoferrin protein" refers to the entire lactoferrin protein molecule. In an embodiment, the lactoferrin protein is a human lactoferrin protein. As used herein, the term "sub-peptide" refers to a peptide comprising a fragment of amino acids from the entire lactoferrin protein molecule. The sub-peptide may be any stretch of amino acids of the lactoferrin protein, including any peptide of two or more amino acids. The sub-peptide may be a single consecutive stretch of amino acids from the lactoferrin protein or may be a combination of two of more stretches of consecutive amino acids from the lactoferrin protein. In an embodiment, the sub-peptide is between 10 and 30 amino acids in length.

The lactoferrin protein may for example be of the following amino acid sequence:

(SEQ ID No. 1)
MKLVFLVLLFLGALGLCLAGRRRRSVQWCAVSQPEATKCFQWQRNMRRVR

GPPVSCIKRDSPIQCIQAIAENRADAVTLDGGFIYEAGLAPYKLRPVAAE

VYGTERQPRTHYYAVAVVKKGGSFQLNELQGLKSCHTGLRRNAGWNVPIG

TLRPFLNWTGPPEPIEAAVARFFSASCVPGADKGQFPNLCRLCAGTGENK

CAFSSQEPYFSYSGAFKCLRDGAGDVAFIRESTVFEDLSDEAERDEYELL

CPDNTRKPVDKFKDCHLARVPSHAVVARSVNGKEDAIWNLLRQAQEKFGK

DKSPKFQLFGSPSGQKDLLFKDSAIGFSRVPPRIDSGLYLGSGYFTAIQN

LRKSEEEVAARRARVVWCAVGEQELRKCNQWSGLSEGSVTCSSASTTEDC

IALVLKGEADAMSLDGGYVYTAGKCGLVPVLAENYKSQQSSDPDPNCVDR

PVEGYLAVAVVRRSDTSLTWNSVKGKKSCHTAVDRTAGWNIPMGLLFNQT

GSCKFDEYFSQSCAPGSDPRSNLCALCIGDEQGENKCVPNSNERYYGYTG

AFRCLAEDAGDVAFVKGVTVLQNTDGNNNEAWAKDLKLADFALLCLDGKR

KPVTEARSCHLAMAPNHAVVSRMDKVERLKQVLLHQQAKFGRNGSDCPDK

FCLFQSETKNLLENDNTECLARLHGKTTYEKYLGPQYVAGITNLKKCSTS

PLLEACEFLRK

In an embodiment, the sub-peptide may be any peptide fragment of SEQ ID No. 1, or any combination of peptide fragments of SEQ ID No. 1. In a particular embodiment, the sub-peptide is of SEQ ID No. 4.

In an embodiment, the lactoferrin protein or sub-peptide thereof may comprise an amino acid sequence having one or more amino acid modifications as compared to a naturally occurring sequence, such as for example as compared to SEQ ID No. 1. In an embodiment, the lactoferrin protein or sub-peptide thereof of the present disclosure has at least 90%, at least 91%, at least 92%, at least 93%, at least 94%, at least 95%, at least 96%, at least 97%, at least 98%, or at least 99% sequence identity over its entire length to the sequence of SEQ ID No. 1 or a fragment thereof. In an embodiment, the lactoferrin protein or sub-peptide thereof of the present disclosure has a sequence that is identical to the sequence of SEQ ID No. 1 or a fragment thereof.

Some embodiments of the present disclosure relate to methods for making a complex between at least one particle of an agent and at least one target cell of a subject for upregulating that subject's production of lactoferrin and/or a sub-peptide of lactoferrin.

In some embodiments of the present disclosure, the agent can be administered to the subject by: an intravenous route, an intramuscular route, an intraperitoneal route, an intrathecal route, an intravesical route, a topical route, an intranasal route, a transmucosal route, a pulmonary route, an oral route or combinations thereof.

In some embodiments of the present disclosure, the agent can be administered to the subject by pipetting a dose of the agent into an in vitro cell culture, perfusing or immersing an ex vivo cell or tissue preparation with a solution that comprises the agent, mixing a biological fluid sample with a solution or substrate that comprises the agent, or combinations thereof.

Some embodiments of the present disclosure relate to an agent that can be administered to a subject with a condition that is associated, either directly or indirectly with the subject forming an adhesion and/or scars. When a therapeutically effective amount of the agent is administered to the subject, the subject may change production and/or functionality of one or more immune-system molecules. For example, the subject may increase production of lactoferrin and/or a sub-peptide of lactoferrin by changing the production of one or more sequences of DNA, one or more sequences of RNA and/or one or more proteins and/or one or more regulatory molecules that regulate the subject's levels of lactoferrin and/or a sub-peptide of lactoferrin.

In some embodiments of the present disclosure, the subject may respond to receiving the therapeutic amount of the agent by changing production of lactoferrin and/or a sub-peptide of lactoferrin by changing production and/or functionality of one or more DNA sequences, one or more RNA sequences, and/or one or more proteins that regulate the levels and/or functionality of the one or more intermediary molecules. The one or more intermediary molecules regulate the subject's levels of lactoferrin and/or a sub-peptide of lactoferrin.

In some embodiments of the present disclosure, the agent can be: a vector used for gene therapy; one or more selected nucleotides, a sequence of nucleotides, one or more nucleosides, a sequence of nucleosides, a RNA complex, a DNA complex or combinations thereof.

In some embodiments of the present disclosure, the agent is a vector that comprises a gene insert, for example a recombinant virus vector (RVV), used for gene therapy. The gene therapy is useful for increasing the production of lactoferrin and/or a sub-peptide of lactoferrin.

In some embodiments, the vector comprises an inverted terminal repeat. The inverted terminal repeat may, for example, comprise a first inverted terminal repeat and a second inverted terminal repeat. In some embodiments, the gene insert is positioned between the first inverted terminal repeat and the second inverted terminal repeat.

The first inverted terminal repeat may, for example, be of the following sequence of SEQ ID No. 2:

```
                                              (SEQ ID No. 2)
CTGCGCGCTCGCTCGCTCACTGAGGCCGCCCGGGCAAAGCCCGGGCGTCG

GGCGACCTTTGGTCGCCCGGCCTCAGTGAGCGAGCGAGCGCGCAGAGAGG

GAGTGGCCAACTCCATCACTAGGGGTTCCT
```

The second inverted terminal repeat may, for example, be of the following sequence of SEQ ID No. 3:

```
                                              (SEQ ID No. 3)
AGGAACCCCTAGTGATGGAGTTGGCCACTCCCTCTCTGCGCGCTCGCTCG

CTCACTGAGGCCGGGCGACCAAAGGTCGCCCGACGCCCGGGCTTTGCCCG

GGCGGCCTCAGTGAGCGAGCGAGCGCGC
```

In an embodiment, the agent is an RVV comprising an insert that encodes for a human lactoferrin protein or a sub-peptide thereof. In an embodiment, the insert is positioned between inverted terminal repeats, such as between the first and second inverted terminal repeats of SEQ ID Nos. 2 and 3.

In some embodiments of the present disclosure, the insert comprises a nucleotide sequence encoding a lactoferrin protein or a sub-peptide thereof linked to an immunoglobulin. The lactoferrin may be a human lactoferrin (e.g., SEQ ID No. 1) or any sub-peptide thereof. In an embodiment, the insert comprises a nucleotide sequence encoding a sub-peptide of lactoferrin having the amino acid sequence of SEQ ID No. 4:

```
                                              (SEQ ID No. 4)
EATKCFQWQRNMRRVRGPPVSCIKR
```

The nucleotide sequence encoding the lactoferrin protein or sub-peptide may be linked directly or indirectly to the nucleotide sequence encoding the immunoglobulin. By "directly", it is meant that the sequences are continuous without intervening nucleotides. By "indirectly", it is meant that there are intervening nucleotides. The intervening nucleotides may, for example, be a linker peptide and/or a hinge peptide. In an embodiment, there are nucleotides encoding a flexible linker peptide and a hinge peptide positioned between nucleotide sequence encoding the lactoferrin protein or sub-peptide and the nucleotide sequence encoding the immunoglobulin.

In an embodiment, the immunoglobulin of the present disclosure is an IgG Fc region. In some embodiments, it is a human IgG Fc region. The IgG Fc region may comprise one or both of a constant heavy 2 (CH2) and a constant heavy 3 (CH3) domain. In an embodiment, the IgG Fc region comprises both a CH2 domain and a CH3 domain. The CH2 and CH3 domain may be of any suitable sequence and, for example, may be of the following amino acid sequences:

CH2 Human IgG:

```
                                              (SEQ ID No. 5)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAK
```

CH3 Human IgG:

```
                                              (SEQ ID No. 6)
GQPREPQVYTLPPSREEMTKNQVSLTCLVKGFYPSDIAVEWESNGQPENN

YKTTPPVLDSDGSFFLYSKLTVDKSRWQQGNVFSCSVMHEALHNHYTQKS

LSLSPGK
```

Thus, in an embodiment, the immunoglobulin of the present disclosure may comprise the amino acid sequence of SEQ ID No. 7:

(SEQ ID No. 7)
APELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPA

PIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHE

ALHNHYTQKSLSLSPGK

In some embodiments of the present disclosure, the insert encoding a lactoferrin protein or a sub-peptide thereof linked to an immunoglobulin may comprise the following nucleotide sequence:

(SEQ ID No. 8)
GAGGCTACCAAGTGTTTTCAGTGGCAGAGGAACATGAGAAAGGTGCGGGG

ACCACCCGTGAGCTGCATCAAGAGGGGATCCGGAGGAGGAGGCAGCGGAG

GAGGCGGATCTGGCGGAGGCGGAAGCGACAAGACCCACACATGCCCACCA

TGTCCTGCTCCAGAGCTGCTGGGAGGACCTTCCGTGTTCCTGTTTCCTCC

AAAGCCAAAGGATACCCTGATGATCAGCAGGACCCCAGAGGTGACATGCG

TGGTGGTGGACGTGTCCCACGAGGACCCCGAGGTGAAGTTCAACTGGTAC

GTGGACGGCGTGGAGGTGCACAACGCTAAGACAAAGCCACGCGAGGAGCA

GTACAACTCCACCTACAGGGTGGTGTCTGTGCTGACAGTGCTGCACCAGG

ATTGGCTGAACGGAAAGGAGTACAAGTGCAAGGTGTCTAACAAGGCCCTG

CCCGCTCCTATCGAGAAGACCATCAGCAAGGCCAAGGGCCAGCCAAGAGA

GCCCCAGGTGTACACACTGCCCCCTTCCCGGGAGGAGATGACCAAGAACC

AGGTGTCTCTGACATGTCTGGTGAAGGGATTCTACCCCTCTGACATCGCT

GTGGAGTGGGAGAGCAACGGCCAGCCTGAGAACAACTACAAGACCACACC

ACCCGTGCTGGACTCCGATGGATCTTTCTTTCTGTACAGCAAGCTGACCG

TGGATAAGTCCAGATGGCAGCAGGGCAACGTGTTTAGCTGCTCCGTGATG

CACGAGGCCCTGCACAACCACTACACACAGAAGTCTCTGAGCCTGTCCCC

CGGCAAG

In some embodiments, the insert may further comprise a nucleotide sequence encoding a signal peptide. Any suitable signal peptide may be used, such as for example a signal peptide that functions to translocate the protein to a cellular membrane and/or toward a particular secretory pathway. In an embodiment of the present disclosure, the signal peptide is a human growth hormone (HGH) signal peptide. The HGH signal peptide may, for example, have the following amino acid sequence:

(SEQ ID No. 9)
MATGSRTSLLLAFGLLCLPWLQEGSA

Thus, in a further embodiment, the nucleotide sequence of the insert may be that of SEQ ID No. 10, which comprises nucleotide sequences encoding an HGH signal, a sub-peptide of the lactoferrin protein and an Fc region (CH2 and CH3 domains):

(SEQ ID No. 10)
ATGGCCACCGGCTCTCGCACAAGCCTGCTGCTGGCTTTCGGACTGCTGTG

CCTGCCTTGGCTCCAGGAGGGCTCCGCCGAGGCTACCAAGTGTTTTCAGT

GGCAGAGGAACATGAGAAAGGTGCGGGGACCACCCGTGAGCTGCATCAAG

AGGGGATCCGGAGGAGGAGGCAGCGGAGGAGGCGGATCTGGCGGAGGCGG

AAGCGACAAGACCCACACATGCCCACCATGTCCTGCTCCAGAGCTGCTGG

GAGGACCTTCCGTGTTCCTGTTTCCTCCAAAGCCAAAGGATACCCTGATG

ATCAGCAGGACCCCAGAGGTGACATGCGTGGTGGTGGACGTGTCCCACGA

GGACCCCGAGGTGAAGTTCAACTGGTACGTGGACGGCGTGGAGGTGCACA

ACGCTAAGACAAAGCCACGCGAGGAGCAGTACAACTCCACCTACAGGGTG

GTGTCTGTGCTGACAGTGCTGCACCAGGATTGGCTGAACGGAAAGGAGTA

CAAGTGCAAGGTGTCTAACAAGGCCCTGCCCGCTCCTATCGAGAAGACCA

TCAGCAAGGCCAAGGGCCAGCCAAGAGAGCCCCAGGTGTACACACTGCCC

CCTTCCCGGGAGGAGATGACCAAGAACCAGGTGTCTCTGACATGTCTGGT

GAAGGGATTCTACCCCTCTGACATCGCTGTGGAGTGGGAGAGCAACGGCC

AGCCTGAGAACAACTACAAGACCACACCCCGTGCTGGACTCCGATGGA

TCTTTCTTTCTGTACAGCAAGCTGACCGTGGATAAGTCCAGATGGCAGCA

GGGCAACGTGTTTAGCTGCTCCGTGATGCACGAGGCCCTGCACAACCACT

ACACACAGAAGTCTCTGAGCCTGTCCCCCGGCAAG

As described herein, in some embodiments the insert may be carried within a plasmid vector, such as an adeno-associated virus vector. The plasmid vector may comprise one or more of the following features.

Some embodiments of the present disclosure include the following nucleotide sequence of SEQ ID No. 11 (a CASI promoter):

(SEQ ID No. 11)
GGAGTTCCGCGTTACATAACTTACGGTAAATGGCCCGCCTGGCTGACCGC

CCAACGACCCCCGCCCATTGACGTCAATAATGACGTATGTTCCCATAGTA

ACGCCAATAGGGACTTTCCATTGACGTCAATGGGTGGAGTATTTACGGTA

AACTGCCCACTTGGCAGTACATCAAGTGTATCATATGCCAAGTACGCCCC

CTATTGACGTCAATGACGGTAAATGGCCCGCCTGGCATTATGCCCAGTAC

ATGACCTTATGGGACTTTCCTACTTGGCAGTACATCTACGTATTAGTCAT

CGCTATTACCATGGTCGAGGTGAGCCCCACGTTCTGCTTCACTCTCCCCA

TCTCCCCCCCCTCCCCACCCCCAATTTTGTATTTATTTATTTTTTAATTA

TTTTGTGCAGCGATGGGGGCGGGGGGGGGGGGGGCGCGCCAGGCGGGG

CGGGGCGGGGCGAGGGGCGGGGCGGGGCGAGGCGGAGAGGTGCGGCGGC

AGCCAATCAGAGCGGCGCGCTCCGAAAGTTTCCTTTTATGGCGAGGCGGC

GGCGGCGGCGGCCCTATAAAAAGCGAAGCGCGCGGCGGGCGGGAGTCGCT

GCGCGCTGCCTTCGCCCCGTGCCCCGCTCCGCCGCCGCCTCGCGCCGCCC

GCCCCGGCTCTGACTGACCGCGTTACTAAAACAGGTAAGTCCGGCCTCCG

CGCCGGGTTTTGGCGCCTCCCGCGGGCGCCCCCCTCCTCACGGCGAGCGC

TGCCACGTCAGACGAAGGGCGCAGCGAGCGTCCTGATCCTTCCGCCCGGA

-continued
CGCTCAGGACAGCGGCCCGCTGCTCATAAGACTCGGCCTTAGAACCCCAG

TATCAGCAGAAGGACATTTTAGGACGGGACTTGGGTGACTCTAGGGCACT

GGTTTTCTTTCCAGAGAGCGGAACAGGCGAGGAAAAGTAGTCCCTTCTCG

GCGATTCTGCGGAGGGATCTCCGTGGGGCGGTGAACGCCGATGATGCCTC

TACTAACCATGTTCATGTTTTCTTTTTTTTCTACAGGTCCTGGGTGACG

AACAG

Some embodiments of the present disclosure include the following nucleotide sequence of SEQ ID No. 12 (a Woodchuck Hepatitis Posttranslational Regulatory Element (WPRE) portion):

(SEQ ID No. 12)
AATCAACCTCTGGATTACAAAATTTGTGAAAGATTGACTGGTATTCTTAA

CTATGTTGCTCCTTTTACGCTATGTGGATACGCTGCTTTAATGCCTTTGT

ATCATGCTATTGCTTCCCGTATGGCTTTCATTTTCTCCTCCTTGTATAAA

TCCTGGTTGCTGTCTCTTTATGAGGAGTTGTGGCCCGTTGTCAGGCAACG

TGGCGTGGTGTGCACTGTGTTTGCTGACGCAACCCCCACTGGTTGGGGCA

TTGCCACCACCTGTCAGCTCCTTTCCGGGACTTTCGCTTTCCCCCTCCCT

ATTGCCACGGCGGAACTCATCGCCGCCTGCCTTGCCCGCTGCTGGACAGG

GGCTCGGCTGTTGGGCACTGACAATTCCGTGGTGTTGTCGGGGAAATCAT

CGTCCTTTCCTTGGCTGCTCGCCTGTGTTGCCACCTGGATTCTGCGCGGG

ACGTCCTTCTGCTACGTCCCTTCGGCCCTCAATCCAGCGGACCTTCCTTC

CCGCGGCCTGCTGCCGGCTCTGCGGCCTCTTCCGCGTCTTCGCCTTCGCC

CTCAGACGAGTCGGATCTCCCTTTGGGCCGCCTCCCCGC

In some embodiments of the present disclosure, the RVV is an adeno-associated virus vector. In a particular embodiment, the present disclosure relates to an RVV of the following nucleotide sequence of SEQ ID No. 13:

(SEQ ID No. 13)
CAGCAGCTGCGCGCTCGCTCGCTCACTGAGGCCGCCCGGGCAAAGCCCGG

GCGTCGGGCGACCTTTGGTCGCCCGGCCTCAGTGAGCGAGCGAGCGCGCA

GAGAGGGAGTGGCCAACTCCATCACTAGGGGTTCCTTGTAGTTAATGATT

AACCCGCCATGCTACTTATCTACGTAGCCATGCTCTAGGACATTGATTAT

TGACTAGTGGAGTTCCGCGTTACATAACTTACGGTAAATGGCCCGCCTGG

CTGACCGCCCAACGACCCCCGCCCATTGACGTCAATAATGACGTATGTTC

CCATAGTAACGCCAATAGGGACTTTCCATTGACGTCAATGGGTGGAGTAT

TTACGGTAAACTGCCCACTTGGCAGTACATCAAGTGTATCATATGCCAAG

TACGCCCCCTATTGACGTCAATGACGGTAAATGGCCCGCCTGGCATTATG

CCCAGTACATGACCTTATGGGACTTTCCTACTTGGCAGTACATCTACGTA

TTAGTCATCGCTATTACCATGGTCGAGGTGAGCCCCACGTTCTGCTTCAC

TCTCCCCATCTCCCCCCCCTCCCCACCCCCAATTTTGTATTTATTTATTT

TTTAATTATTTTGTGCAGCGATGGGGGCGGGGGGGGGGGGGGCGCGCGC

CAGGCGGGGCGGGCGGGGCGAGGGGCGGGGCGGGGCGAGGCGGAGAGGT

GCGGCGGCAGCCAATCAGAGCGGCGCGCTCCGAAAGTTTCCTTTTATGGC

-continued
GAGGCGGCGGCGGCGGCGGCCCTATAAAAAGCGAAGCGCGCGGCGGGCGG

GAGTCGCTGCGCGCTGCCTTCGCCCCGTGCCCCGCTCCGCCGCCGCCTCG

CGCCGCCCGCCCCGGCTCTGACTGACCGCGTTACTAAAACAGGTAAGTCC

GGCCTCCGCGCCGGGTTTTGGCGCCTCCCGCGGGCGCCCCCCTCCTCACG

GCGAGCGCTGCCACGTCAGACGAAGGGCGCAGCGAGCGTCCTGATCCTTC

CGCCCGGACGCTCAGGACAGCGGCCCGCTGCTCATAAGACTCGGCCTTAG

AACCCCAGTATCAGCAGAAGGACATTTTAGGACGGGACTTGGGTGACTCT

AGGGCACTGGTTTTCTTTCCAGAGAGCGGAACAGGCGAGGAAAAGTAGTC

CCTTCTCGGCGATTCTGCGGAGGGATCTCCGTGGGGCGGTGAACGCCGAT

GATGCCTCTACTAACCATGTTCATGTTTTCTTTTTTTTCTACAGGTCCT

GGGTGACGAACAGGGTACCGCCACCATGGCCACCGGCTCTCGCACAAGCC

TGCTGCTGGCTTTCGGACTGCTGTGCCTGCCTTGGCTCCAGGAGGGCTCC

GCCGAGGCTACCAAGTGTTTTCAGTGGCAGAGGAACATGAGAAAGGTGCG

GGGACCACCCGTGAGCTGCATCAAGAGGGGATCCGGAGGAGGAGGCAGCG

GAGGAGGCGGATCTGGCGGAGGCGGAAGCGACAAGACCCACACATGCCCA

CCATGTCCTGCTCCAGAGCTGCTGGGAGGACCTTCCGTGTTCCTGTTTCC

TCCAAAGCCAAAGGATACCCTGATGATCAGCAGGACCCCAGAGGTGACAT

GCGTGGTGGTGGACGTGTCCCACGAGGACCCCGAGGTGAAGTTCAACTGG

TACGTGGACGGCGTGGAGGTGCACAACGCTAAGACAAAGCCACGCGAGGA

GCAGTACAACTCCACCTACAGGGTGGTGTCTGTGCTGACAGTGCTGCACC

AGGATTGGCTGAACGGAAAGGAGTACAAGTGCAAGGTGTCTAACAAGGCC

CTGCCCGCTCCTATCGAGAAGACCATCAGCAAGGCCAAGGGCCAGCCAAG

AGAGCCCCAGGTGTACACACTGCCCCCTTCCCGGGAGGAGATGACCAAGA

ACCAGGTGTCTCTGACATGTCTGGTGAAGGGATTCTACCCCTCTGACATC

GCTGTGGAGTGGGAGAGCAACGGCCAGCCTGAGAACAACTACAAGACCAC

ACCACCCGTGCTGGACTCCGATGGATCTTTCTTTCTGTACAGCAAGCTGA

CCGTGGATAAGTCCAGATGGCAGCAGGGCAACGTGTTTAGCTGCTCCGTG

ATGCACGAGGCCCTGCACAACCACTACACACAGAAGTCTCTGAGCCTGTC

CCCCGGCAAGTGACTCTAGAATAATCAACCTCTGGATTACAAAATTTGTG

AAAGATTGACTGGTATTCTTAACTATGTTGCTCCTTTTACGCTATGTGGA

TACGCTGCTTTAATGCCTTTGTATCATGCTATTGCTTCCCGTATGGCTTT

CATTTTCTCCTCCTTGTATAAATCCTGGTTGCTGTCTCTTTATGAGGAGT

TGTGGCCCGTTGTCAGGCAACGTGGCGTGGTGTGCACTGTGTTTGCTGAC

GCAACCCCCACTGGTTGGGCATTGCCACCACCTGTCAGCTCCTTTCCGG

GACTTTCGCTTTCCCCCTCCCTATTGCCACGGCGGAACTCATCGCCGCCT

GCCTTGCCCGCTGCTGGACAGGGCTCGGCTGTTGGGCACTGACAATTCC

GTGGTGTTGTCGGGGAAATCATCGTCCTTTCCTTGGCTGCTCGCCTGTGT

TGCCACCTGGATTCTGCGCGGGACGTCCTTCTGCTACGTCCCTTCGGCCC

TCAATCCAGCGGACCTTCCTTCCCGCGGCCTGCTGCCGGCTCTGCGGCCT

CTTCCGCGTCTTCGCCTTCGCCCTCAGACGAGTCGGATCTCCCTTTGGGC

```
CGCCTCCCCGCCTAAGCTTATCGATACCGTCGAGATCTAACTTGTTTATT
GCAGCTTATAATGGTTACAAATAAAGCAATAGCATCACAAATTTCACAAA
TAAAGCATTTTTTTCACTGCATTCTAGTTGTGGTTTGTCCAAACTCATCA
ATGTATCTTATCATGTCTGGATCTCGACCTCGACTAGAGCATGGCTACGT
AGATAAGTAGCATGGCGGGTTAATCATTAACTACAAGGAACCCCTAGTGA
TGGAGTTGGCCACTCCCTCTCTGCGCGCTCGCTCGCTCACTGAGGCCGGG
CGACCAAAGGTCGCCCGACGCCCGGGCTTTGCCCGGGCGGCCTCAGTGAG
CGAGCGAGCGCGCCAGCTGGCGTAATAGCGAAGAGGCCCGCACCGATCGC
CCTTCCCAACAGTTGCGCAGCCTGAATGGCGAATGGAATTCCAGACGATT
GAGCGTCAAAATGTAGGTATTTCCATGAGCGTTTTTCCTGTTGCAATGGC
TGGCGGTAATATTGTTCTGGATATTACCAGCAAGGCCGATAGTTTGAGTT
CTTCTACTCAGGCAAGTGATGTTATTACTAATCAAAGAAGTATTGCGACA
ACGGTTAATTTGCGTGATGGACAGACTCTTTTACTCGGTGGCCTCACTGA
TTATAAAAACACTTCTCAGGATTCTGGCGTACCGTTCCTGTCTAAAATCC
CTTTAATCGGCCTCCTGTTTAGCTCCCGCTCTGATTCTAACGAGGAAAGC
ACGTTATACGTGCTCGTCAAAGCAACCATAGTACGCGCCCTGTAGCGGCG
CATTAAGCGCGGCGGGTGTGGTGGTTACGCGCAGCGTGACCGCTACACTT
GCCAGCGCCCTAGCGCCCGCTCCTTTCGCTTTCTTCCCTTCCTTTCTCGC
CACGTTCGCCGGCTTTCCCCGTCAAGCTCTAAATCGGGGGCTCCCTTTAG
GGTTCCGATTTAGTGCTTTACGGCACCTCGACCCCAAAAAACTTGATTAG
GGTGATGGTTCACGTAGTGGGCCATCGCCCTGATAGACGGTTTTTCGCCC
TTTGACGTTGGAGTCCACGTTCTTTAATAGTGGACTCTTGTTCCAAACTG
GAACAACACTCAACCCTATCTCGGTCTATTCTTTTGATTTATAAGGGATT
TTGCCGATTTCGGCCTATTGGTTAAAAAATGAGCTGATTTAACAAAAATT
TAACGCGAATTTTAACAAAATATTAACGTTTACAATTTAAATATTTGCTT
ATACAATCTTCCTGTTTTTGGGGCTTTTCTGATTATCAACCGGGGTACAT
ATGATTGACATGCTAGTTTTACGATTACCGTTCATCGATTCTCTTGTTTG
CTCCAGACTCTCAGGCAATGACCTGATAGCCTTTGTAGAGACCTCTCAAA
AATAGCTACCCTCTCCGGCATGAATTTATCAGCTAGAACGGTTGAATATC
ATATTGATGGTGATTTGACTGTCTCCGGCCTTTCTCACCCGTTTGAATCT
TTACCTACACATTACTCAGGCATTGCATTTAAAATATATGAGGGTTCTAA
AAATTTTTATCCTTGCGTTGAAATAAAGGCTTCTCCCGCAAAAGTATTAC
AGGGTCATAATGTTTTGGTACAACCGATTTAGCTTTATGCTCTGAGGCT
TTATTGCTTAATTTTGCTAATTCTTTGCCTTGCCTGTATGATTTATTGGA
TGTTGGAATTCCTGATGCGGTATTTTCTCCTTACGCATCTGTGCGGTATT
TCACACCGCATATGGTGCACTCTCAGTACAATCTGCTCTGATGCCGCATA
GTTAAGCCAGCCCCGACACCCGCCAACACCCGCTGACGCGCCCTGACGGG
CTTGTCTGCTCCCGGCATCCGCTTACAGACAAGCTGTGACCGTCTCCGGG
AGCTGCATGTGTCAGAGGTTTTCACCGTCATCACCGAAACGCGCGAGACG
AAAGGGCCTCGTGATACGCCTATTTTTATAGGTTAATGTCATGATAATAA
TGGTTTCTTAGACGTCAGGTGGCACTTTTCGGGGAAATGTGCGCGGAACC
```
```
CCTATTTGTTTATTTTTCTAAATACATTCAAATATGTATCCGCTCATGAG
ACAATAACCCTGATAAATGCTTCAATAATATTGAAAAAGGAAGAGTATGA
GTATTCAACATTTCCGTGTCGCCCTTATTCCCTTTTTTGCGGCATTTTGC
CTTCCTGTTTTTGCTCACCCAGAAACGCTGGTGAAAGTAAAAGATGCTGA
AGATCAGTTGGGTGCACGAGTGGGTTACATCGAACTGGATCTCAACAGCG
GTAAGATCCTTGAGAGTTTTCGCCCCGAAGAACGTTTTCCAATGATGAGC
ACTTTTAAAGTTCTGCTATGTGGCGCGGTATTATCCCGTATTGACGCCGG
GCAAGAGCAACTCGGTCGCCGCATACACTATTCTCAGAATGACTTGGTTG
AGTACTCACCAGTCACAGAAAAGCATCTTACGGATGGCATGACAGTAAGA
GAATTATGCAGTGCTGCCATAACCATGAGTGATAACACTGCGGCCAACTT
ACTTCTGACAACGATCGGAGGACCGAAGGAGCTAACCGCTTTTTTGCACA
ACATGGGGGATCATGTAACTCGCCTTGATCGTTGGGAACCGGAGCTGAAT
GAAGCCATACCAAACGACGAGCGTGACACCACGATGCCTGTAGCAATGGC
AACAACGTTGCGCAAACTATTAACTGGCGAACTACTTACTCTAGCTTCCC
GGCAACAATTAATAGACTGGATGGAGGCGGATAAAGTTGCAGGACCACTT
CTGCGCTCGGCCCTTCCGGCTGGCTGGTTTATTGCTGATAAATCTGGAGC
CGGTGAGCGTGGGTCTCGCGGTATCATTGCAGCACTGGGGCCAGATGGTA
AGCCCTCCCGTATCGTAGTTATCTACACGACGGGGAGTCAGGCAACTATG
GATGAACGAAATAGACAGATCGCTGAGATAGGTGCCTCACTGATTAAGCA
TTGGTAACTGTCAGACCAAGTTTACTCATATATACTTTAGATTGATTTAA
AACTTCATTTTTAATTTAAAAGGATCTAGGTGAAGATCCTTTTTGATAAT
CTCATGACCAAAATCCCTTAACGTGAGTTTTCGTTCCACTGAGCGTCAGA
CCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGT
TTGCCGGATCAAGAGCTACCAACTCTTTTTCCGAAGGTAACTGGCTTCAG
CAGAGCGCAGATACCAAATACTGTCCTTCTAGTGTAGCCGTAGTTAGGCC
ACCACTTCAAGAACTCTGTAGCACCGCCTACATACCTCGCTCTGCTAATC
CTGTTACCAGTGGCTGCTGCCAGTGGCGATAAGTCGTGTCTTACCGGGTT
GGACTCAAGACGATAGTTACCGGATAAGGCGCAGCGGTCGGGCTGAACGG
GGGGTTCGTGCACACAGCCCAGCTTGGAGCGAACGACCTACACCGAACTG
AGATACCTACAGCGTGAGCTATGAGAAAGCGCCACGCTTCCCGAAGGGAG
AAAGGCGGACAGGTATCCGGTAAGCGGCAGGGTCGGAACAGGAGAGCGCA
CGAGGGAGCTTCCAGGGGGAAACGCCTGGTATCTTTATAGTCCTGTCGGG
TTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGG
CCTTTTGCTGGCCTTTTGCTCACATGTTCTTTCCTGCGTTATCCCCTGAT
TCTGTGGATAACCGTATTACCGCCTTTGAGTGAGCTGATACCGCTCGCCG
CAGCCGAACGACCGAGCGCAGCGAGTCAGTGAGCGAGGAAGCGGAAGAGC
GCCCAATACGCAAACCGCCTCTCCCCGCGCGTTGGCCGATTCATTAATG
```

As will be readily appreciated, any of the nucleotide sequences disclosed herein may be modified by routine methods to provide a human codon optimized variant thereof. Different organisms exhibit bias towards the use of certain codons over others for the same amino acid. Human codon optimization involves engineering a particular nucleotide sequence to use synonymous codons to improve protein production in humans.

In similar manner, any of the nucleotide sequences disclosed herein may have a modified sequence based on the degeneracy of codons. As will be appreciated, various different nucleotide sequences are capable of encoding the same protein or peptide, including the protein and peptide sequences of the present disclosure based on the redundancy of the genetic and the degeneracy of codons. In embodiments of the present disclosure, the nucleotide sequence of any agent herein, including the RVV of SEQ ID No. 13 or any nucleotide sequence therein may have an alternate sequence based on degeneracy of the genetic code.

Thus, in an embodiment, the nucleotide sequence encoding the lactoferrin protein or sub-peptide thereof and the immunoglobulin may be a human codon optimized variant thereof, such as a human codon optimized variant of SEQ ID No. 8. In other embodiments, the nucleotide sequence encoding the lactoferrin protein or sub-peptide thereof and the immunoglobulin may be a nucleotide sequence that is different from SEQ ID No. 8 based on degeneracy of the genetic code.

In an embodiment, the nucleotide sequence encoding the HGH signal peptide, lactoferrin protein or sub-peptide thereof and the immunoglobulin may be a human codon optimized variant thereof, such as a human codon optimized variant of SEQ ID No. 10 or 13. In other embodiments, the nucleotide sequence encoding the HGH signal peptide, lactoferrin protein or sub-peptide thereof and the immunoglobulin may be a nucleotide sequence that is different from SEQ ID Nos. 10 or 13 based on degeneracy of the genetic code.

In another embodiment, the present disclosure relates to a fusion protein comprising a human lactoferrin protein or a sub-peptide thereof linked to an immunoglobulin. The human lactoferrin protein or sub-peptide thereof may be any of those described herein, including in some embodiments comprising or consisting of the sequence of SEQ ID No. 4. The immunoglobulin may likewise be any of those described herein, including in some embodiments being an IgG Fc region comprising the CH2 and CH3 domains of SEQ ID No. 5 and 6, respectively.

In an embodiment, the fusion protein comprises the amino acid sequences of SEQ ID No. 4, 5 and 6. In an embodiment, the sequences are ordered 4-5-6 from N-Terminus to C-Terminus. In an embodiment, there are intervening amino acids between SEQ ID No. 4 and 5.

In some embodiments, the fusion protein may further comprise a signal peptide. Without limitation, the signal peptide may be a HGH signal peptide. The signal peptide may be any of those described herein, including in some embodiments comprising or consisting of the sequence of SEQ ID No. 9.

In an embodiment, the fusion protein comprises the amino acid sequences of SEQ ID Nos. 4, 5, 6 and 9. In an embodiment, the sequences are ordered 9-4-5-6 from N-Terminus to C-Terminus. In an embodiment, there are intervening amino acids between SEQ ID Nos. 4 and 5.

In some embodiments, the fusion protein may further comprise a peptide linker and/or a hinge (e.g., an antibody heavy chain hinge). For example, in the above embodiments, the intervening amino acids may be one or both of a peptide linker and/or a hinge.

In an embodiment, the fusion protein comprises the amino acid sequence of SEQ ID No. 14:

```
                                              (SEQ ID No. 14)
EATKCFQWQRNMRRVRGPPVSCIKRGSGGGGSGGGGSGGGGSDKTHTCPP

CPAPELLGGPSVFLFPPKPKDTLMISRTPEVTCVVVDVSHEDPEVKENWY

VDGVEVHNAKTKPREEQYNSTYRVVSVLTVLHQDWLNGKEYKCKVSNKAL

PAPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVM

HEALHNHYTQKSLSLSPGK
```

In an embodiment, the fusion protein comprises the amino acid sequence of SEQ ID No. 15:

```
                                              (SEQ ID No. 15)
MATGSRTSLLLAFGLLCLPWLQEGSAEATKCFQWQRNMRRVRGPPVSCIK

RGSGGGGSGGGGSGGGGSDKTHTCPPCPAPELLGGPSVFLFPPKPKDTLM

ISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLP

PSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK
```

In the above embodiments of fusion proteins of SEQ ID Nos. 14 and 15, there is an exemplary linker peptide of amino acid sequence GSGGGGSGGGGSGGGGS (SEQ ID No. 14) and an exemplary hinge of amino acid sequence DKTHTCPPCP (SEQ ID No. 15).

In some embodiments of the present disclosure, the agent is a virus that can be within one or more of the following genus: flavivirus, influenza, enterovirus, rotavirus, rubellavirus, rubivirus, morbillivirus, orthopoxvirus, varicellovirus, dependoparvovirus, alphabaculovirus, betabaculovirus, deltabaculovirus, gammabaculovirus, mastadenovirus, simplexvirus, varicellovirus, cytomegalovirus, or combinations thereof.

Some embodiments of the present disclosure also relate to administering a therapeutically effective amount of the agent. The therapeutically effective amount of the agent will not substantially increase or advance any deleterious conditions within the subject. For example, the therapeutically effective amount will not cause cytokinesis, hypercytokinemia, or any other uncontrolled, or partially controlled, upregulation of the subject's immune system. In some embodiments of the present disclosure, the therapeutically effective amount of the agent that is administered to a patient is between about 10 and about $1 \times 10^{16}$ TCID50/kg (50% tissue culture infective dose per kilogram of the patient's body weight). In some embodiments of the present disclosure the therapeutically effective amount of the agent that is administered to the patient is about $1 \times 10^{13}$ TCID$_{50}$/kg. In some embodiments of the present disclosure, the therapeutically effective amount of the agent that is administered to a patient is measured in TPC/kg (total particle count of the agent per kilogram of the patient's body weight). In some embodiments the therapeutically effective amount of the agent is between about 10 and about $1 \times 10^{16}$ TCP/kg.

Some embodiments of the present disclosure relate to a method for making a complex within a subject. The method comprises a step of administering a therapeutically effective amount of the agent to the subject. The complex comprises at least one particle of the agent, and one or more target cells. When the complex is formed, it affects a change in metabolism of the one or more target cells that may result in the subject upregulating the production of lactoferrin and/or a sub-peptide of lactoferrin. Examples of a target cell include, but are not limited to: an adrenal gland cell, a B cell, a bile duct cell, a chondrocyte, a cochlear cell, a corneal cell, an endocardium cell, an endometrial cell, an endothelial cell, an epithelial cell, an eosinophil, a fibroblast, a hair follicle cell, a hepatocyte, a keratinocyte, a lymph node cell, a neutrophil, a macrophage, a mucosal cell, a myocyte, a neuron, a glomeruli cell, an optic nerve cell, an osteoblast, an ovarian tissue cell, a pancreatic islet beta cell, a pericardium cell, a platelet, a red blood cell (RBC), a retinal cell, a scleral cell, a Schwann cell, a T cell, a testicular tissue cell, a thyroid gland cell, an uveal cell, or combinations thereof.

Some embodiments of the present disclosure relate to a therapy that can be administered to a subject with the condition. The therapy comprises a step of administering to the subject a therapeutically effective amount of an agent that will upregulate production of lactoferrin or a sub-peptide of lactoferrin. When the therapy is administered to a patient, the therapy will promote the in vivo production of lactoferrin and/or a sub-peptide of lactoferrin.

Some embodiments of the present disclosure relate to a method of treating a condition where the method comprises a step of administering to the subject a therapeutically effective amount of an agent that will upregulate production of lactoferrin and/or a sub-peptide of lactoferrin.

Example 1

In one example, the agent is a gene vector that includes a gene insert for the gene responsible for producing lactoferrin protein in humans. In this example, the gene insert produces a biological compound with the following amino-acid sequence (SEQ ID No. 1):

MKLVFLVLLFLGALGLCLAGRRRRSVQWCAVSQPEATKCFQWQRNMRRVR

GPPVSCIKRDSPIQCIQAIAENRADAVTLDGGFIYEAGLAPYKLRPVAAE

VYGTERQPRTHYYAVAVVKKGGSFQLNELQGLKSCHTGLRRNAGWNVPIG

TLRPFLNWTGPPEPIEAAVARFFSASCVPGADKGQFPNLCRLCAGTGENK

CAFSSQEPYFSYSGAFKCLRDGAGDVAFIRESTVFEDLSDEAERDEYELL

CPDNTRKPVDKFKDCHLARVPSHAVVARSVNGKEDAIWNLLRQAQEKFGK

DKSPKFQLFGSPSGQKDLLFKDSAIGFSRVPPRIDSGLYLGSGYFTAIQN

LRKSEEEVAARRARVVWCAVGEQELRKCNQWSGLSEGSVTCSSASTTEDC

IALVLKGEADAMSLDGGYVYTAGKCGLVPVLAENYKSQQSSDPDPNCVDR

PVEGYLAVAVVRRSDTSLTWNSVKGKKSCHTAVDRTAGWNIPMGLLFNQT

GSCKFDEYFSQSCAPGSDPRSNLCALCIGDEQGENKCVPNSNERYYGYTG

AFRCLAEDAGDVAFVKGVTVLQNTDGNNNEAWAKDLKLADFALLCLDGKR

-continued

KPVTEARSCHLAMAPNHAVVSRMDKVERLKQVLLHQQAKFGRNGSDCPDK

FCLFQSETKNLLENDNTECLARLHGKTTYEKYLGPQYVAGITNLKKCSTS

PLLEACEFLRK

Example 2—Expression Cassette

An expression cassette for expressing an exemplary sub-peptide of human lactoferrin in a subject cell was synthesized by Genscript. The exemplary lactoferrin sub-peptide was a synthetic peptide based on the antibacterial region of human lactoferrin, namely HLD1 (EATKCFQWQRNMRKVRGPPVSCIKR; SEQ ID No. 4). The expression cassette contained nucleotide sequences encoding a lactoferrin-Fc fusion peptide comprising a human growth hormone (HGH) signal peptide (MATGSRT-SLL LAFGLLCLPWLQEGSA; SEQ ID No. 9) and the HLD1 peptide of SEQ ID No: 4 linked via a flexible peptide linker and hinge to the CH2 and CH3 domains of a human IgG Fc-region having the amino acid sequences of SEQ ID Nos. 5 and 6, respectively. The synthesized expression cassette for the lactoferrin-Fc fusion peptide was cloned into the pAVA-00200 plasmid backbone containing the CASI promoter 1, multiple cloning site (MCS), Woodchuck Hepatitis Virus post-transcriptional regulatory element (WPRE), Simian virus 40 (SV40) polyadenylation (polyA) sequence all flanked by the AAV2 inverted terminal repeats (ITR).

pAVA-00200 was cut with the restriction enzymes KpnI and XbaI in the MCS and separated on a 1% agarose gel. The band of interest was excised and purified using a gel extraction kit. Each BLP expression cassette was amplified by PCR using Taq polymerase and the PCR products were gel purified and the bands on interest were also excised and purified using a gel extraction kit. These PCR products contained the lactoferrin-Fc fusion peptide expression cassette in addition to 15 base pair 5' and 3' overhangs that align with the ends of the linearized pAVA-00200 backbone. Using in-fusion cloning 2, the amplified lactoferrin-Fc fusion peptide expression cassette was integrated with the pAVA-00200 backbone via homologous recombination. The resulting plasmid vector contained at least the following: 5' ITR, a CASI promoter, the lactoferrin-Fc fusion peptide expression cassette, WPRE, and a 3' ITR, per SEQ ID No. 13.

Example 3—Experimental Data

The ovarian bursa of C57BL/6 mice were implanted with $1 \times 10^6$ ID8 epithelial carcinoma cells. About 60 days later, eight mice were administered intramuscularly $1 \times 10^{10}$ 50 mM of phosphate buffered saline (control group) or $1 \times 10^{10}$ vg of the AAV comprising SEQ ID No. 13 (treatment group). Serum samples were obtained from animals in the control group and the treatment group. The serum samples were analyzed using a quantitative ELISA to measure lactoferrin-Fc fusion peptide levels. The analysis of the serum samples from the animals in the control group showed that no lactoferrin-Fc fusion peptide was detected.

FIG. 1 shows the levels of lactoferrin-Fc fusion peptide (μg/mL) detected in the serum samples from the animals in the treatment group up to 77 days following the treatment.

Figure 2:
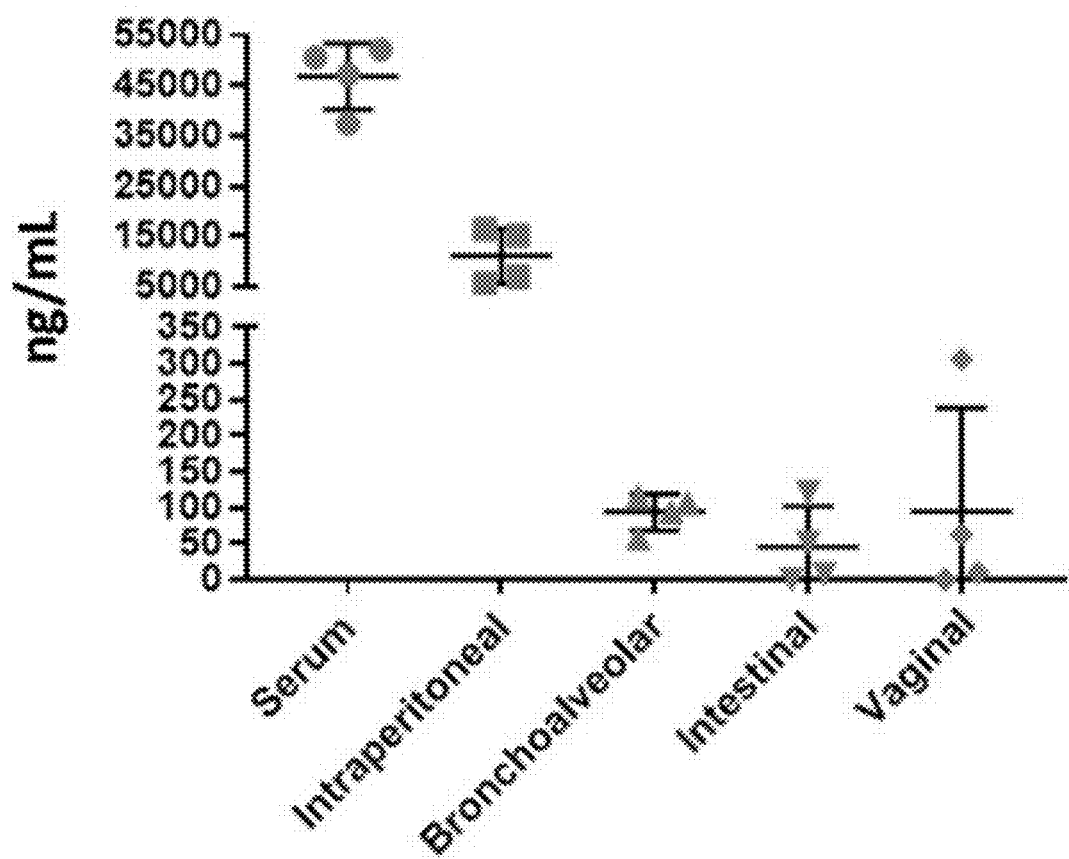
FIG. 2 is a scatter plot that shows lactoferrin-Fc fusion peptide levels at mucosal surfaces (lavage fluid) and in serum at 77 days following administration of a vector according to embodiments of the present disclosure.

FIG. 2 shows the levels of lactoferrin-Fc fusion peptide (ng/mL) detected at mucosal surfaces (lavage fluid) and in serum at 77 days after treatment. Intraperitoneal lavage volume was 1000 μL, bronchoalveolar lavage volume was 800 μL, intestinal lavage volume was 1000 μL and vaginal lavage volume was 150 μL.

Figure 3:
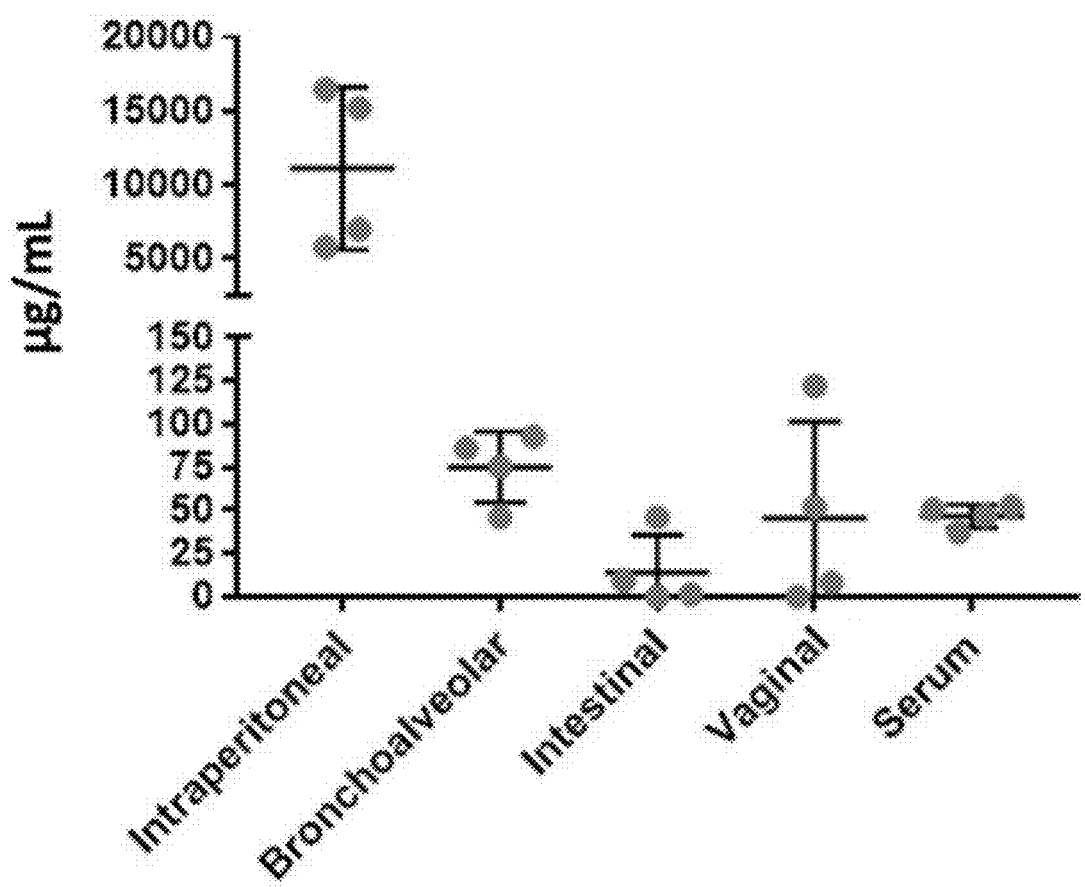
FIG. 3 is a scatter plot that shows systemic endpoint concentration of lactoferrin-Fc fusion peptide (μg/mL) following administration of a vector according to embodiments of the present disclosure.

FIG. 3 shows the systemic endpoint concentration of lactoferrin-Fc fusion peptide (μg/mL).

---

The invention claimed is:

1. A recombinant virus vector (RVV), the RVV comprising:
   a) a nucleotide sequence encoding a human lactoferrin protein or a sub-peptide thereof linked to an immunoglobulin;
   b) an inverted terminal repeat; and
   c) a nucleotide sequence encoding a human growth hormone (HGH) signal peptide.

2. The RVV of claim 1, wherein the inverted terminal repeat is SEQ ID NO: 2 or SEQ ID NO: 3.

3. The RVV of claim 1, wherein the inverted terminal repeat is a first inverted terminal repeat of SEQ ID NO: 2 and a second inverted terminal repeat of SEQ ID NO: 3, and wherein the nucleotide sequence encoding the human lactoferrin protein or sub-peptide thereof linked to the immunoglobulin is positioned between the first inverted terminal repeat and the second inverted terminal repeat.

4. The RVV of claim 1, wherein the sub-peptide of the human lactoferrin protein comprises the amino acid sequence of SEQ ID NO: 4.

5. The RVV of claim 1, wherein the immunoglobulin comprises a human IgG Fc region.

6. The RVV of claim 5, wherein the human IgG Fc region comprises a CH2 domain and a CH3 domain.

7. The RVV of claim 6, wherein the CH2 domain comprises the amino acid sequence of SEQ ID NO: 5 and the CH3 domain comprises the amino acid sequence of SEQ ID NO: 6.

8. The RVV of claim 1, wherein the human lactoferrin protein or sub-peptide thereof comprises the amino acid sequence of SEQ ID NO: 4 and the immunoglobulin comprises the amino acid sequence of SEQ ID NO: 7.

9. The RVV of claim 1, wherein the nucleotide sequence encoding the human lactoferrin protein, or sub-peptide thereof, when linked to the immunoglobulin comprises the sequence of SEQ ID NO: 8 or a human codon optimized variant thereof, wherein the nucleotide sequence of SEQ ID NO. 8 encodes a fusion protein comprising the sub-peptide of the human lactoferrin protein and the immunoglobulin.

10. The RVV of claim 1, wherein the HGH signal peptide comprises the amino acid sequence of SEQ ID NO: 9.

11. The RVV of claim 10, wherein RVV comprises the nucleotide sequence of SEQ ID NO: 10 or a human codon optimized variant thereof.

12. The RVV of claim 1, wherein the RVV is an adeno-associated virus vector.

13. The RVV of claim 1, wherein the RVV comprises the nucleotide sequence of SEQ ID NO: 13 or a human codon optimized variant thereof.

14. A pharmaceutical composition comprising the RVV of claim 1 and one or more pharmaceutically acceptable carriers and/or one or more excipients.

* * * * *

UNITED STATES PATENT AND TRADEMARK OFFICE
CERTIFICATE OF CORRECTION

| | | |
|---|---|---|
| PATENT NO. | : 11,891,429 B2 | |
| APPLICATION NO. | : 17/320661 | |
| DATED | : February 6, 2024 | |
| INVENTOR(S) | : Bradley G. Thompson | |

It is certified that error appears in the above-identified patent and that said Letters Patent is hereby corrected as shown below:

On the Title Page

Item (63), delete "Continuation" and insert --Continuation-in-part-- therefor.

Signed and Sealed this
Fifth Day of March, 2024

*Katherine Kelly Vidal*

Katherine Kelly Vidal
*Director of the United States Patent and Trademark Office*